United States Patent
Odrljin

(10) Patent No.: US 10,603,361 B2
(45) Date of Patent: Mar. 31, 2020

(54) METHODS OF TREATING A SUBJECT WITH AN ALKALINE PHOSPHATASE DEFICIENCY

(71) Applicant: Alexion Pharmaceuticals, Inc., New Haven, CT (US)

(72) Inventor: Tatjana Odrljin, Brookline, MA (US)

(73) Assignee: Alexion Pharmaceuticals, Inc., Boston, MA (US)

(*) Notice: Subject to any disclaimer, the term of this patent is extended or adjusted under 35 U.S.C. 154(b) by 96 days.

(21) Appl. No.: 15/544,063

(22) PCT Filed: Jan. 28, 2016

(86) PCT No.: PCT/US2016/015366
§ 371 (c)(1),
(2) Date: Jul. 17, 2017

(87) PCT Pub. No.: WO2016/123342
PCT Pub. Date: Aug. 4, 2016

(65) Prior Publication Data
US 2018/0333470 A1    Nov. 22, 2018

Related U.S. Application Data

(60) Provisional application No. 62/108,669, filed on Jan. 28, 2015.

(51) Int. Cl.
| | |
|---|---|
| A61K 38/46 | (2006.01) |
| A61P 3/00 | (2006.01) |
| A61K 31/137 | (2006.01) |
| A61K 45/06 | (2006.01) |

(52) U.S. Cl.
CPC .......... A61K 38/465 (2013.01); A61K 31/137 (2013.01); A61K 38/46 (2013.01); A61K 45/06 (2013.01); A61P 3/00 (2018.01); C12Y 301/03001 (2013.01)

(58) Field of Classification Search
None
See application file for complete search history.

(56) References Cited

U.S. PATENT DOCUMENTS

| | | |
|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

International Preliminary Report on Patentability for International Patent Application No. PCT/US2016/049983, dated Sep. 11, 2018 (9 pages).
Sequence 4, U.S. Appl. No. 12/599,679, retrieved Nov. 17, 2018 (2 pages).
Agochukwu et al., "Hearing loss in syndromic craniosynostoses: introduction and consideration of mechanisms," Am J Audiol. 23(2): 135-41 (2014).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).

(Continued)

*Primary Examiner* — Iqbal H Chowdhury
(74) *Attorney, Agent, or Firm* — Clark & Elbing LLP

(57) ABSTRACT

Disclosed herein are methods for treating a subject with an alkaline phosphatase deficiency, further comprising monitoring additional anaiytes, e.g., calcium, parathyroid hormone and/or vitamin D, with treatment modifications as indicated by the levels, e.g., serum levels, of the additional anaiytes.

22 Claims, 11 Drawing Sheets

Specification includes a Sequence Listing.

(56) References Cited

U.S. PATENT DOCUMENTS

| | | |
|---|---|---|
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,988,620 B2 | 6/2018 | Crine et al. |
| 10,000,532 B2 | 6/2018 | Crine et al. |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0023652 A1* | 1/2009 | Bell ............... A61K 38/17 514/11.8 |
| 2009/0053192 A1* | 2/2009 | Millan ............... A61K 31/519 424/94.6 |
| 2009/0069243 A1 | 3/2009 | Burnett, Jr. et al. |
| 2009/0092582 A1 | 4/2009 | Bogin et al. |
| 2009/0142347 A1 | 6/2009 | Milian |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1* | 12/2013 | Crine ............... A61K 38/465 424/134.1 |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 | 3/2007 |
| EP | 1759710 A1 | 3/2007 |
| EP | 2158319 | 3/2010 |
| EP | 2158319 B1 | 12/2011 |
| JP | H0870875 A | 3/1996 |
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |

(56) References Cited

FOREIGN PATENT DOCUMENTS

| | | |
|---|---|---|
| JP | 2010-530222 A | 9/2010 |
| JP | 2011-504506 A | 2/2011 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116263 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/134084 A2 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013071262 A1 | 5/2013 |
| WO | WO-2015/112015 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |

OTHER PUBLICATIONS

Barvencik et al., "Skeletal mineralization defects in adult hypophosphatasia—a clinical and histological analysis," Osteoporosis Int. 22(10):2667-75 (2011).

Baumgartner-Sigl et al., "Pyridoxine-responsive seizures as the first symptom of infantile hypophosphatasia caused by two novel missense mutations (c.677T>C, p.M226T; c.1112C>T, p.T371I) of the tissue-nonspecific alkaline phosphatase gene," Bone. 40(6):1655-61 (2007).

Beck et al., "Whole-body MRI in the childhood form of hypophosphatasia," Rheumatol Int. 31(10):1315-20 (2011).

Beederman et al., "Molecular basis of cranial suture biology and disease: osteoblastic and osteoclastic perspectives," Genes Dis. 1(1):120-5 (2014).

Boulet et al., "A population-based study of craniosynostosis in metropolitan Atlanta, 1989-2003," Am J Med Genet A. 146(8):984-91 (2008).

Chan et al., "Endoscope-assisted versus open repair of craniosynostosis: a comparison of perioperative cost and risk," J Craniofac Surg. 24(1): 170-4 (2013).

Choi et al., "Craniosynostosis in growing children: pathophysiological changes and neurosurgical problems," J Korean Neurosurg Soc. 59(3):197-203 (2016).

Chong et al., "Minimally invasive suturectomy and postoperative helmet therapy: advantages and limitations," J Korean Neurosurg Soc. 59(3):227-32 (2016).

Clarke, "Normal bone anatomy and physiology," Clin J Am Soc Nephrol. 3 Suppl 3: S131-9 (2008).

Colantonio et al., "Closing the gaps in pediatric laboratory reference intervals: a CALIPER database of 40 biochemical markers in a healthy and multiethnic population of children," Clin Chem. 58(5):854-68 (2012).

(56) References Cited

OTHER PUBLICATIONS

Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugia. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-159 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: craniosynostosis," BBA Clin. 6:165-76 (2016).
Khanna et al., "Pictorial essay: The many faces of craniosynostosis," Indian J Radiol Imaging. 21(1):49-56 (2011).
Kim et al., "Craniosynostosis: Updates in radiologic diagnosis," J Korean Neurosurg Soc. 59(3):219-26 (2016).
Kozlowski et al., "Hypophosphatasia," Pediatr Radiol. 5(2):103-17 (1976).
Krakow et al., "Clinical and radiographic delineation of Bent Bone Dysplasia-FGFR2 type or Bent Bone Dysplasia with Distinctive Clavicles and Angel-shaped Phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-274 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c. 1559delT in ALPL, a common mutation resulting in the perinatal (lethal) form of hypophosphatasia in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Act Med Litu. 22(2):111-21 (2015).
Anderson, "Mechanism of Mineral Formation in Bone," *Pathology Reviews*. Emanuel Rubin and Ivan Damjanov, 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz, and T. John Martin, 1573-98 (2008).
Whyte, Chapter 22: Hypophosphatasia, *Genetics of Bone Biology and Skeletal Disease*. Rajesh V. Thakker, Michael P. Whyte, John A. Eisman, and Takashi Igarashi, 337-360 (2013).
Del Angel et al., "Birth prevalence estimation of severe Hypophosphatasia in European populations using large-scale protein-coding genetic variation databases," ASHG 2016, Oct. 18-22, Vancouver, Canada. Poster 1670T (2016).
Rockman-Greenberg et al., 16th Annual Clinical Genetics Meeting, Mar. 25-29, Tampa, Florida. (2009).
Simmons, "Best Practices In: Recognizing and Diagnosing Hypophosphatasia," MDedge Endocrinology, <https://www.mdedge.

(56) References Cited

OTHER PUBLICATIONS com/sites/default/files/issues/articles/Alexion_10_11_Final_Web. pdf>, retrieved on Mar. 27, 2019 (8 pages).
Weber et al., "Burden of disease in children with hypophosphatasia: results from patient-reported surveys," ICCBH, Jun. 27-30, 2015, Salzburg, Austria. Poster P119 (2015).
Whyte et al., Pediatric Academic Societies and Asian Society for Pediatric Research Joint Meeting, May 3-6, Vancouver, BC, Canada. Poster 69 (2014).
Whyte et al., European Calcified Tissue Society Congress, May 17-20, Prague, Czech Republic. Poster P364 (2014).
Whyte et al., "A retrospective, multi-national, non-interventional, natural history study of the childhood form of hypophosphatasia," ENDO, Mar. 5-8, 2015, San Diego, California. Abstract LB-OR01-4 (2015).
Stoll et al., "Severe hypophosphatasia due to mutations in the tissue-nonspecific alkaline phosphatase (TNSALP) gene," Genet Couns. 13(3):289-95.
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-116 (2018).
Dortschy, Reinhard, et al. "Bevölkerungsbezogene verteilungswerte ausgewählter laborparameter aus der studie zur gesundheit von kindern und jugendlichen in Deutschland (KiGGS)." (2009).
Communication pursuant to Rule 164(2)(b) and Article 94(3) EPC for European Patent Application 16707571.2, dated Feb. 26, 2019 (12 pages).
Fong et al., "Hypocalcemia: Updates in diagnosis and management for primary care", Can Fam Physician. 58(2):158-62 (2012).
Makras et al., "Medical treatment of Hypercalcaemia", Hormones 8(2):83-95 (2009).
Official Action for Japanese Application No. 2017-539393, dated Sep. 17, 2019 (7 pages).
Invitation to Pay Additional Fees for International Patent Application No. PCT/US2016/015366, dated Jun. 1, 2016 (7 pages).
Weninger et al., "Biochemical and morphological effects of human hepatic alkaline phosphatase in a neonate with hypophosphatasia," Acta Paediatr Scand. Suppl. 360:154-160 (1989).
Whyte et al., "Enzyme-replacement therapy in life-threatening hypophosphatasia," N Engl J Med. 366(10):904-13 (2012).
Ali et al., "Isolation and characterization of calcifying matrix vesicles from epiphyseal cartilage," Proc Natl Acad Sci USA. 67(3):1513-1520 (1970).
Anderson et al., "Pyrophosphate stimulation of calcium uptake into cultured embryonic bones. Fine structure of matrix vesicles and their role in calcification," Dev Biol. 34:211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-837 (2005).
Beertsen et al., "Root development in mice lacking functional tissue non-specific alkaline phosphatase gene: Inhibition of acellular cementum formation," J Dent Res. 78(6):1221-1229 (1999) (10 pages).
Bennett et al., "Extracellular domain-IgG fusion proteins for three human natriuretic peptide receptors," J Biol Chem. 266(34):23060-23067 (1991).
Bernard, "Ultrastructural localization of alkaline phosphatase in initial intramembranous osteogenesis," Clin Orthop Relat Res. 135:218-225 (1978).
Bonilla, "Pharmacokinetics of immunoglobulin administered via intravenous or subcutaneous routes," Immunol Allergy Clin N Am. 28:803-819 (2008).
Byers et al., "Effect of enzyme replacement therapy on bone formation in a feline model of mucopolysaccharidosis type VI," Bone. 21(5):425-431 (1997).

Cameron et al., "Minireview: Natriuretic peptides during development of the fetal heart and circulation," Endocrinology. 144(6):2191-2194 (2003).
Clemens et al., "Pharmacokinetics and biological actions of subcutaneously administered human brain natriuretic peptide," J Pharmacol Exp Ther. 287(1):67-71 (1998).
Declaration of Dr. Philippe Crine for EP 08757088.3, executed Jan. 14, 2011 (6 pages).
Engel et al., "Characterization of the hormone binding site of natriuretic peptide receptor-C," FEBS Lett. 360:169-172 (1995).
Extended European Search Report for European Application No. 08757088.3, dated Jun. 21, 2010 (6 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Garg, Investigation of the role of FcRn in the absorption, distribution, and elimination of monoclonal antibodies. Dissertation: State University of New York at Buffalo, 2007 (Abstract only) (2 pages).
Greenberg et al., "A homoallelic Gly$^{317}$ to Asp mutation in *ALPL* causes the perinatal (lethal) form of hypophosphatasia in Canadian mennonites," Genomics. 17:215-217 (1993).
Harmey et al., "Concerted regulation of inorganic pyrophosphate and osteopontin by *Akp2, Enpp1*, and *Ank*," Am J Pathol. 164(4):1199-1209 (2004).
Harmey et al., "Elevated skeletal osteopontin levels contribute to the hypophosphatasia phenotype in *Akp2*$^{-/-}$ mice," J Bone Miner Res. 21(9):1377-1386 (2006).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Hessle et al., "Tissue-nonspecific alkaline phosphatase and plasma cell membrane glucoprotein-1 are central antagonistic regulators of bone mineralization," Proc Natl Acad Sci USA. 99(14): 9445-9449 (2002).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kochendoerfer, "Protein & peptide drug delivery—third international conference: Minimally invasive delivery methods," Sep. 22-23, Philadelphia, PA. IDrugs. 6(11):1043-1045 (2003).
Kostenuik et al., "Infrequent delivery of a long-acting PTH-Fc fusion protein has potent anabolic effects on cortical and cancellous bone," J Bone Miner Res. 22(10):1534-1547 (2007).
Mahmood et al., "Selection of the first-time dose in humans: comparison of different approaches based on interspecies scaling of clearance," J Clin Pharmacol. 43:692-697 (2003).
Millan, "Mammalian Alkaline Phosphatases," Wiley-WCH Verlag GmbH & Co., Weinheim, Germany, 1-322 (2006).
Morris et al., "Immunolocalization of alkaline phosphatase in osteoblasts and matrix vesicles of human fetal bone," Bone Miner. 19:287-298 (1992).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAF64516. Retrieved on Apr. 16, 2013 (2 pages).
NCBI Protein Database Accession No. AAC33858. Retrieved on Apr. 16, 2013 (1 page).

(56) References Cited

OTHER PUBLICATIONS

NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI26166. Retrieved on Apr. 16, 2013 (2 pages).
NCBI Protein Database Accession No. AAI18209. Retrieved on Apr. 17, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798.1, downloaded on Apr. 17, 2013. (2 pages).
NCBI Protein Database Accession No. NP_112603. Retrieved on Apr. 16, 2013 (3 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q9N0V0. Retrieved on Apr. 16, 2013 (1 page).
Nosjean et al., "Human tissue non-specific alkaline phosphatases: sugar-moiety-induced enzymic and antigenic modulations and genetic aspects," Biochem J. 321:297-303 (1997).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharmaceutical Res. 14(7):911-916 (1997).
Tye et al., "Delineation of the hydroxyapatite-nucleating domains of bone sialoprotein," J Biol Chem. 278(10):7949-7955 (2003).
Urlaub et al., "Deletion of the diploid dihydrofolate reductase locus from cultured mammalian cells," Cell. 33:405-412 (1983).
Wang et al., "A mouse model for achondroplasia produced by targeting fibroblast growth factor receptor 3," Proc Natl Acad Sci USA. 96:4455-4460 (1999).
Wang et al., "Structure-based chemical modification strategy for enzyme replacement treatment of phenylketonuria," Mol Genet Metab. 86:134-140 (2005).
Weiss et al., "A missense mutation in the human liver/bone/kidney alkaline phosphatase gene causing a lethal form of hypophosphatasia," Proc Natl Acad Sci USA. 85:7666-7669 (1988).

Whyte et al., "Markedly increased circulating pyridoxal-5'-phosphate levels in hypophosphatasia," J Clin Invest. 76:752-756 (1985).
Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
International Preliminary Report on Patentability for International Patent Application No. PCT/CA2011/050258, dated Nov. 15, 2012 (9 pages).
International Search Report and Written Opinion for International Patent Application No. PCT/US2012/039004, dated Nov. 2, 2012 (22 pages).
Invitation to Pay Additional Fees for International Patent Application No. PCT/US2012/039004, dated Aug. 29, 2012 (2 pages).
Oikawa et al., "Enzyme replacement therapy on hypophosphatasia mouse model," J Inherit Metab Dis. 9 pages (2013).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Achord et al., "Human beta-glucuronidase: in vivo clearance and in vitro uptake by a glycoprotein recognition system on reticuloendothelial cells," Cell 15(1):269-278 (1978).
Anderson et al., "Matrix vesicles in osteomalacic hypophosphatasia bone contain apatite-like mineral crystals," Am J Pathol. 151(6):1555-61 (1997).
Barton et al., "Replacement therapy for inherited enzyme deficiency—macrophage-targeted glucocerebrosidase for Gaucher's disease," N Engl J Med. 324(21):1464-70 (1991) (abstract only).
Bernardi, "Chromatography of proteins on hydroxyapatite," Methods Enzymol. 27:471-9 (1973).
Boskey et al., "Matrix vesicles promote mineralization in a gelatin gel," Calcif Tissue Int 60(3):309-15 (1997).
Ciancaglini et al., "Contribution of matrix vesicles and alkaline phosphatase to ectopic bone formation," Braz. J Med Biol Res. 39(5):603-10 (2006).
Crawley et al., "Enzyme replacement therapy in a feline model of Maroteaux-Lamy Syndrome," J Clin Invest. 97(8):1864-73 (1996).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Eng et al., "Safety and efficacy of recombinant human alpha-galactosidase A—replacement therapy in Fabry's disease," N Engl J Med. 345(1):9-16 (2001).
Gilbert et al., "Chimeric peptides of statherin and osteopontin that bind hydroxyapatite and mediate cell adhesion," J Biol Chem. 275(21):16213-8 (2000).
Guo et al., "Protein tolerance to random amino acid change," Proc Natl Acad Sci USA. 101(25):9205-9210 (2004).
Henthorn et al., "Missense mutations of the tissue-nonspecific alkaline phosphatase gene in hypophosphatasia," Clin Chem. 38(12):2501-5 (1992).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Kakkis et al., "Enzyme-replacement therapy in mucopolysaccharidosis I," N Engl J Med. 344(3):182-8 (2001).
Kaufmann et al., "Influence of low temperature on productivity, proteome and protein phosphorylation of CHO cells," Biotechnol Bioeng. 63(5):573-82 (1999).

(56) References Cited

OTHER PUBLICATIONS

Milián et al., "Enzyme replacement therapy for murine hypophosphatasia," J Bone Miner Res. 23(6): 777-87 (2008).
Murray, "Lectin-specific targeting of lysosomal enzymes to reticuloendothelial cells," Methods Enzymol. 149:25-42 (1987).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Pedersen et al., "Removal of N-terminal polyhistidine tags from recombinant proteins using engineered aminopeptidases," Protein Expr Purif. 15(3):389-400 (1999).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Sekido et al., "Novel drug delivery system to bone using acidic oligopeptide: pharmacokinetic characteristics and pharmacological potential," J Drug Target. 9(2):111-21 (2001).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Tomatsu, Declaration Under 37 C.F.R. § 1.132 for U.S. Appl. No. 11/484,870, dated Jun. 1, 2009 (3 pages).
Uludag et al., "Bone affinity of a bisphosphonate-conjugated protein in vivo," Biotechnol Prog. 16(6):1115-8 (2000).
Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "Isolation and characterization of a cDNA encoding a human liver/bone/kidney-type alkaline phosphatase," Proc Natl Acad Sci USA. 83(19):7182-6 (1986).
Weiss et al., "Structure of the human liver/bone/kidney alkaline phosphatase gene," J Biol Chem. 263(24):12002-10 (1988).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte et al., "Hypophosphatasia," in the Metabolic and Molecular Bases of Inherited Disease (4th ed.), pp. 5313-5329, 2001 (McGraw-Hill Book Company) (epub pp. 1-41).
Whyte et al., "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).
Whyte et al., "Marrow cell transplantation for infantile hypophosphatasia," J Bone Miner Res. 18(4):624-36 (2003).
Yamamoto et al., "Prolonged survival and phenotypic correction of Akp2(-/-) hypophosphatasia mice by lentiviral gene therapy," J Bone Miner Res. 26(1):135-42 (2011).
Communication from Examining Division for European Application No. EP 05 73 9065.0, dated Jun. 18, 2009 (6 pages).
Communication from Examining Division for European Application No. EP 05 73 9065.0, dated Jun. 11, 2010 (5 pages).
Office Action for U.S. Appl. No. 12/793,517, dated Aug. 16, 2010 (9 pages).

Office Action for U.S. Appl. No. 13/071,445, dated Feb. 6, 2012 (12 pages).
Supplementary European Search Report for European Application No. EP 05 73 9065 (date of completion of search Nov. 7, 2008, dated Dec. 2, 2008) (3 pages).
Choe et al., "Substrate profiling of cysteine proteases using a combinatorial peptide library identifies functionally unique specificities," J Biol Chem. 281(18):12824-12832 (2006).
Official Action for Japanese Application No. 2013-544989, dated Oct. 27, 2015 (3 pages).
Harris, "The human alkaline phosphatases: what we know and what we don't know," Clin Chim Acta. 186:133-50 (1989).
De la Croix Ndong et al., "Asfotase-alpha improves bone growth, mineralization and strength in mouse models of neurofibromatosis type-1," Nat Med. 20(8):904-10 (2014) (10 pages).
International Search Report and Written Opinion for International Patent Application No. PCT/US2016/047166, dated Nov. 7, 2016 (15 pages).
Ratner, "Alexion pays big for Synageva's rare disease drug candidate," Nat Biotechnol. 33(7):679 (2015).
Addison et al., "Pyrophosphate inhibits mineralization of osteoblast cultures by binding to mineral, up-regulating osteopontin, and inhibiting alkaline phosphatase activity," J Biol Chem. 282(21):15872-15883 (2007).
Advisory Action for U.S. Appl. No. 11/484,870, dated Dec. 20, 2007 (4 pages).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," *Am J Pathol*. 164:841-847 (2004).
Barranger et al., "Lessons learned from the development of enzyme therapy for Gaucher disease," J Inherit Metab Dis. 24(Supp 2):89-96 (2001).
Bobé et al., "Fas-mediated liver damage in MRL hemopoietic chimeras undergoing lpr-mediated graft-versus-host disease," J Immunol. 159:4197-4204 (1997).
Boskey, "Amorphous calcium phosphate: The contention of bone," J Dent Res. 76:1433-1436 (1997).
Campbell et al., "Insulin-like growth factor (IGF)-binding protein-5-(201-218) region regulates hydroxyapatite and IGF-I binding," Am J Physiol. 273:E1005-1013 (1997).
Cleland et al., "Emerging protein delivery methods," Curr Opin Biotechnol. 12:212-219 (2001).
Communication from Examining Division for European Application No. EP 08 757 088.3, dated Apr. 20, 2011 (4 pages).
Data Sheet for pFUSE-SEAP-hFC "Plasmid designed for the expression of a SEAP-Fc Fusion protein," Invivogen, San Diego, CA (4 pages) (1989).
Extended European Search Report for European Application No. 11774253.6, dated Oct. 14, 2013 (8 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Hailing Linder et al., "Glycosylation differences contribute to distinct catalytic properties among bone alkaline phosphotase isoforms," available in PMC Nov. 1, 2010, published in final edited form as: Bone. 45(5):987-993 (2009) (17 pages).
Hardy et al., "Dissection of a carboxy-terminal region of the yeast regulatory protein RAP1 with effects on both transcriptional activation and silencing," Mol Cell Biol. 12(3):1209-1217 (1992).

(56) References Cited

OTHER PUBLICATIONS

Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Ikezawa, "Glycosylphosphatidylinositol (GPI)-anchored proteins," *Biol Pharm Bull*. 25(4):409-417 (2002).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
Kasugai et al., "Selective drug delivery system to bone: small peptide $(Asp)_6$ conjugation," J Bone Miner Res. 15(5):936-943 (2000).
Leone et al., "Allosteric modulation of pyrophosphatase activity of rat osseous plate alkaline phosphatase by magnesium ions," Int J Biochem Cell Biol. 30:89-97 (1998).
Meyer, "Can biological calcification occur in the presence of pyrophosphate?" Arch Biochem Biophys. 231:1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Moss et al., "Association of inorganic-pyrophosphatase activity with human alkaline-phosphatase preparations," Biochem J. 102:53-57 (1967).
Murshed et al., "Unique coexpression in osteoblasts of broadly expressed genes accounts for the spatial restriction of ECM mineralization to bone," Genes Dev. 19:1093-1104 (2005).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. Q6PYX1. Retrieved on Oct. 15, 2013 (2 pages).
Ngo et al., Computational complexity, protein structure prediction, and the levinthal paradox. *The Protein Folding Problem and Tertiary Structure Prediction*. Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).

Office Action for U.S. Appl. No. 11/484,870, dated Feb. 2, 2009 (16 pages).
Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 13/071,445, dated May 25, 2012 (14 pages).
Official Notification and Search Report for Eurasian Patent Application No. 201291138, dated May 17, 2013 (3 pages).
Patti et al., "Critical residues in the ligand-binding site of the *staphylococcus aureus* collagen-binding adhesin (MSCRAMM)," J Biol Chem. 270(20):12005-12011 (1995).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).
Spears et al., "Deoxyuridylate effects on thymidylate synthase-5-fluorodeoxyuridylate-folate ternary complex formation," Biochem Pharmacol. 38(18):2985-2993 (1989).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Extended European Search Report for European Application No. EP 08757088, date of completion Jun. 7, 2010 (6 pages).
Symersky et al., "Structure of the collagen-binding domain from a *Staphylococcus aureus* adhesin," Nat Struct Biol. 4(10):833-838 (1997).
Tomatsu, Declaration Under 37 C.F.R. § 1.132 for U.S. Appl. No. 11/484,870, dated Nov. 27, 2007 (2 pages).
Whyte, "Hypophosphatasia and the role of alkaline phosphatase in skeletal mineralization," Endocr Rev. 15(4):439-461 (1994).
Whyte, "Hypophosphatasia: Nature's window on alkaline phosphatase function in man," *Principles of Bone Biology*, 2nd ed., Bilezikian, Raisz, and Rodan. 2:1229-1248 (2002).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Orimo, "The mechanism of mineralization and the role of alkaline phosphatase in health and disease," J Nippon Med Sch. 77(1):4-12 (2010).
Attwood, "The Babel of Bioinformatics," Genomics. 290(5491):471-3 (2000).

(56) References Cited

OTHER PUBLICATIONS

Skolnick et al., "From genes to protein structure and function: novel applications of computational approaches in the genomic era," Trends Biotechnol. 18(1):34-9 (2000).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-1525 (1999).
Chusho et al., "Dwarfism and early death in mice lacking C-type natriuretic peptide," Proc Natl Acad Sci USA. 98(7):4016-4021 (2001).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
Furuya et al., "Structural requirements of C-type natriuretic peptide for elevation of cyclic GMP in cultured vascular smooth muscle cells," Biochem Biophys Res Commun. 183(3):964-969 (1992).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Horton et al., "Achondroplasia," Lancet. 370:162-172, 2007.
Inoue et al., "Four functionally distinct C-type natriuretic peptides found in fish reveal evolutionary history of the natriuretic peptide system," Proc Natl Acad Sci USA. 100(17):10079-10084 (2003).
International Search Report and Written Opinion for International Patent Application No. PCT/CA2011/050807, dated Apr. 13, 2012 (18 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Kalra et al., "The role of C-type natriuretic peptide in cardiovascular medicine," Eur Heart J. 22:997-1007 (2001).
Lo et al., "High level expression and secretion of Fc-X fusion proteins in mammalian cells," Protein Eng. 11(6):495-500 (1998).
Mericq et al., "Regulation of fetal rat bone growth by C-type natriuretic peptide and cGMP," Pediatr Res. 47(2):189-193 (2000) (9 pages).
Miyazawa et al., "Cyclic GMP-dependent protein kinase II plays a critical role in C-type natriuretic estide-mediated endochondral ossification," Endocrinology. 143(9):3604-3610 (2002).
Nakao et al., "The pharmacokinetics of alpha-human atrial natriuretic polypeptide in healthy subjects," Eur J Clin Pharmacol. 31:101-103 (1986).
NCBI Protein Database Accession No. XP_001109717. Retrieved on Apr. 17, 2013 (1 page).
Pfeifer et al., "Intestinal secretory defects and dwarfism in mice lacking cGMP-dependent protein kinase II," Science. 274:2082-2086 (1996).
Potter et al., "Natriuretic peptides, their receptors, and cyclic guanosine monophosphate-dependent signaling functions," Endocr Rev. 27(1):47-72 (2006).
Shukla et al., "RNA interference and inhibition of MEK-ERK signaling prevent abnormal skeletal phenotypes in a mouse model of craniosynostosis," Nat Genet. 39(9):1145-1150 (2007).
Suda et al., "C-type natriuretic peptide as an autocrine/paracrine regulator of osteoblast: evidence for possible presence of bone natriuretic peptide system," Biochem Biophys Res Commun. 223:1-6 (1996).
Takano et al., "Molecular evolution of shark C-type natriuretic peptides," Zoolog Sci. 11:451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Wang et al., "Mice lacking Nf1 in osteochondroprogenitor cells display skeletal dysplasia similar to patients with neurofibromatosis type 1," Hum Mol Genet. 20(20):3910-3924 (2011).
Williams et al., "Solute transport in growth plate cartilage: In vitro and in vivo," Biophys J. 93(3):1039-1050 (2007).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in Ibab -/- mice," Peptides. 29(9):1575-1581 (2008).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Husain et al., "Fc site-specific labeling of immunoglobulins with calf intestinal alkaline phosphatase," Bioconjug Chem. 5(5):482-90 (1994).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
Yasoda et al., "Overexpression of CNP in chondrocytes rescues achondroplasia through a MAPK-dependent pathway," Nat Med. 10(1):80-86 (2004).
EBI Blast for Accession No. ATD17216. Entered Oct. 16, 2008 (1 page).
Supplementary European Search Report for European Patent Application No. 11853820.6, dated Mar. 25, 2014 (3 pages).
International Preliminary Report on Patentability for International Patent Application No. PCT/US2012/060869, dated Apr. 22, 2014 (7 pages).
International Preliminary Report on Patentability for International Patent Application No. PCT/US2012/039004, dated Apr. 22, 2014 (8 pages).
Siris et al., "Paget's disease of bone," Trends Endocrinol Metab. 2(6):207-12 (1991).
European Search Report for European Patent Application No. 12842640.0, dated Mar. 13, 2015 (7 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Nahabet et al., "Postnatal Pancraniosynostosis in a Patient With Infantile Hypophosphatasia," Cleft Palate Craniofac J. 53(6):741-4 (2016).
International Search Report and Written Opinion for International Patent Application No. PCT/US2015/058498, dated Jan. 22, 2016 (12 pages).

(56) References Cited

OTHER PUBLICATIONS

Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).
Madson et al., "Asfotase alfa: sustained efficacy and tolerability in children with hypophosphatasia treated for 5 years," ESPE Abstracts. 84:FC2.4 (2015) (2 pages).
Center for Drug Evaluation and Research, "Application No. 125513Orig1s000," <http://www.accessdata.fda.gov/drugsatfda_docs/nda/2015/125513Orig1s000MedR.pdf>, review completed Oct. 20, 2015; retrieved on Jun. 1, 2016 (254 pages).
International Search Report and Written Opinion for International Patent Application No. PCT/US2016/025721, dated Aug. 17, 2016 (18 pages).
Phillips et al., "A modified performance-oriented mobility assessment tool for assessing clinically relevant gait impairments and change in children with hypophosphatasia: development and validation," Bone Abstracts. 4 P136 (2015).
Highlights of Prescribing Information for Strensig™, Alexion Pharmaceuticals, Inc., available <http://www.alexion.com/Documents/strensiq_pi-10-2015.aspx>, 2015 (19 pages).
Phillips et al., "Gait assessment in children with childhood hypophosphatasia: impairments in muscle strength and physical function," The Endocrine Society's 97th Annual Meeting & Expo, Mar. 5-8, 2015, San Diego, California (2 pages).
"View of NCT02235493 on Nov. 19, 2015," ClinicalTrials.gov archive, Nov. 19, 2015 (4 pages).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Austria, Salzburg. Bone Abstracts. 4: OC18 (2015) (3 pages).
International Search Report and Written Opinion for International Patent Application No. PCT/US2016/039595, dated Feb. 21, 2017 (16 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Appeal Brief as Filed in U.S. Appl. No. 12/638,527, mailed Oct. 9, 2015 (101 pages).
Reply Brief as Filed in U.S. Appl. No. 12/638,527, mailed Apr. 22, 2016 (4 pages).
Examiner's Answer to Appeal Brief for U.S. Appl. No. 12/638,527, mailed Feb. 23, 2016 (9 pages).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Millán et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
International Search Report and Written Opinion for International Patent Application No. PCT/US2017/025590, dated Jun. 29, 2017 (18 pages).

Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ahn et al., "Idiopathic calcium pyrophosphate dihydrate (CPPD) crystal deposition disease in a young male patient: a case report," J Korean Med Sc. 18(6):917-20 (2003).
Cahill et al., "Infantile hypophosphatasia: transplantation therapy trial using bone fragments and cultured osteoblasts,"J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)—>Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).
Spentchian et al., "Severe hypophosphatasia: characterization of fifteen novel mutations in the ALPL gene," Hum Mutat. 22(1) (2003) (5 pages).
Takinami et al., "The mutant (F310L and V365I) tissue-nonspecific alkaline phosphatase gene from hypophosphatasia," J Med Dent Sci. 51(1):67-74 (2004).
Sawai et al., "Severe perinatal hypophosphatasia due to homozygous deletion of T at nucleotide 1559 in the tissue nonspecific alkaline phosphatase gene,". Prenat Diagn. 23(9):743-6 (2003).
Wickramasinghe et al., "A case of hypophosphatasia," Ceylon Med J. 48(3):94-5 (2003).
Yamamoto et al., "A successful treatment with pyridoxal phosphate for West syndrome in hypophosphatasia," Pediatr Neurol. 30(3):216-8 (2004).
International Preliminary Report on Patentability for International Patent Application No. PCT/US2016/015366, dated Aug. 10, 2017 (10 pages).
International Search Report and Written Opinion for International Patent Application No. PCT/US2017/047527, dated Nov. 6, 2017 (10 pages).
Millán et al., "Hypophosphatasia—pathophysiology and treatment," available in PMC Sep. 22, 2014, published in final edited form as: Actual Osteol. 8(3):164-182 (2012) (21 pages).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Mornet et al., "Structural evidence for a functional role of human tissue nonspecific alkaline phosphatase in bone mineralization," J Biol Chem. 276(33):31171-8 (2001).
Bhattacharyya et al., "Hypophosphatasia and the risk of atypical femur fractures: a case-control study," BMC Muscoloskelet Disord. 17:332 (2016) (4 pages).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop et al., "Transformative therapy in hypophosphatasia," Arch Dis Child. 101(6):514-5 (2016).
Bishop, "Clinical management of hypophosphatasia," Clin Cases Miner Bone Metab. 12(2):170-3 (2015).
Durussel et al., "Bone mineralization-dependent craniosynostosis and craniofacial shape abnormalities in the mouse model of infantile hypophosphatasia," Dev Dyn. 245(2):175-82 (2016).
Braunstein, "Multiple fractures, pain, and severe disability in a patient with adult-onset hypophosphatasia," Bone Rep. 4:1-4 (2015).
Bloch-Zupan, "Hypophosphatasia: diagnosis and clinical signs—a dental surgeon perspective," Int J Paediatr Dent. 26(6):426-438 (2016).
Kishnani et al., "Monitoring guidance for patients with hypophosphatasia treated with asfotase alfa," Mol Genet Metab. 122(1-2):4-17 (2017).

(56) References Cited

OTHER PUBLICATIONS

Güzel et al., "Pyridoxine-responsive seizures in infantile hypophosphatasia and a novel homozygous mutation in ALPL gene," J Clin Res Pediatr Endocrinol. 8(3):360-4 (2016).
Gasque et al., "Improvement of the skeletal and dental hypophosphatasia phenotype in Alpl -/- mice by administration of soluble (non-targeted) chimeric alkaline phosphatase," Available in PMC Mar. 1, 2016, published in final edited form as: Bone. 72:137-147 (2015) (25 pages).
Fodor et al., "Differencial diagnosis of the low alkaline phosphatase activities," Orv Hetil. 158(26): 1003-1007 (2017) (Article in Hungarian) (English Abstract included).
McKiernan et al., "Clinical and radiographic findings in adults with persistent hypophosphatasemia," J Bone Miner Res. 29(7):1651-60 (2014).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Orimo, "Pathophysiology of hypophosphatasia and the potential role of asfotase alfa," Ther Clin Risk Manag. 12:777-86 (2016).
Morrow, "Expensive new biologic helps children fight hypophosphatasia," Manag Care. 24(12) (2015) (7 pages).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Remde et al., "Successful asfotase alfa treatment in an adult dialysis patient with childhood-onset hypophosphatasia," J Endoc Soc. 1(9):1188-93 (2017).
Panesar, "Hypophosphatasia: a rare disorder," US Pharm. 42(5) (2017) (8 pages).
Padidela et al., "Enzyme-replacement therapy in life-threatening perinatal hypophosphatasia in a premature infant," Endocrine Abstracts. 33:P9 (2013) (1 page).
Sotillo et al., "Signs and symptoms of hypophosphatasia," Dimensions of Dental Hygiene. 15(4):44-47 (2017) (6 pages).
Simm et al., "Successful use of enzyme replacement therapy in infantile hypophosphatasia," J Paediatr Child Health. 53(9):925-926 (2017).
Sheikh et al., "A newborn with no bones: neonatal hypophosphatasia with respiratory distress," J Pediatr. 188:306 (2017).
Saglam et al., "Clinical and genetic findings of Turkish hypophosphatasia cases," J Clin Res Pediatr Endocrinol. 9(3):229-236 (2017).
Whyte et al., "Asfotase alfa treatment improves survival for perinatal and infantile hypophosphatasia," J Clin Endocrinol Metab. 101(1):334-42 (2016) (17 pages).
Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).

Alexion Third Quarter 2017 Earnings Call, "http://files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Urlaub et al., "Isolation of Chinese hamster cell mutants deficient in dihydrofolate reductase activity," Proc Natl Acad Sci U S A. 77(7):4216-20 (1980).
Graham et al., "Characteristics of a human cell line transformed by DNA from human adenovirus type 5," J Gen Virol. 36(1):59-72 (1977).
Mather, "Establishment and characterization of two distinct mouse testicular epithelial cell lines," Biol Reprod. 23(1):243-52 (1980).
Le Du et al., "Crystal structure of alkaline phosphatase from human placenta at 1.8 A resolution. Implication for a substrate specificity," J Biol Chem. 276(12):9158-65 (2001) (9 pages).
Stec et al., "A revised mechanism for the alkaline phosphatase reaction involving three metal ions,", J Mol Biol. 299(5):1303-11 (2000).
Alexion, "Highlights of Prescribing Information" for Strensiq®, 2018 (8 pages).
European Collection of Authenticated Cell Cultures (ECACC) Accession No. 85110503. Retrieved May 2, 2018 (3 pages).
UniProtKB Accession No. P05186. Retrieved May 2, 2018 (19 pages).
UniProtKB Accession No. P01857. Retrieved May 2, 2018 (13 pages).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Recombinant enzyme replacement therapy in hypophosphatasia," Subcell Biochem. 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).
Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).

(56) References Cited

OTHER PUBLICATIONS

Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its useinthe USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).
Takahashi et al., "Parental serum alkaline phosphatase activity as an auxiliary tool for prenatal diagnosis of hypophosphatasia," Prenat Diagn. 37(5):491-6 (2017).
Tenorio et al., "Molecular and clinical analysis of ALPL in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French) (English Abstract Included).
Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
International Search Report and Written Opinion for International Patent Application No. PCT/US2016/054013, dated Dec. 13, 2016 (19 pages).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).
International Search Report and Written Opinion for International Patent Application No. PCT/US2018/020859, dated Jun. 19, 2018 (14 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Matsumoto et al., "Rescue of severe infantile hypophosphatasia mice by AAV-mediated sustained expression of soluble alkaline phosphatase," Hum Gene Ther. 22(11):1355-64 (2011).
Hofmann et al., "Clinical aspects of hypophosphatasia: an update," Clinic Rev Bone Miner Metab. 11(2):60-70 (2013).
Taketani et al., "Clinical and genetic aspects of hypophosphatasia in Japanese patients," Arch Dis Child. 99(3):211-5 (2014) (6 pages).
Whyte, "Physiological role of alkaline phosphatase explored in hypophosphatasia," Ann N Y Acad Sci. 1192:190-200 (2010).
Hofmann et al., "Compound heterozygosity of two functional null mutations in the ALPL gene associated with deleterious neurological outcome in an infant with hypophosphatasia," Bone. 55:150-7 (2013).
de Roo et al., "Infantile hypophosphatasia without bone deformities presenting with severe pyridoxine-resistant seizures," Molecular Genetics and Metabolism 111(3):404-7 (2014).
International Search Report and Written Opinion for International Patent Application No. PCT/US2015/064003, dated Mar. 31, 2016 (13 pages).
Lazdunski et al., "Structure-function relationships for some metalloalkaline phosphatases of E. coli," Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
International Search Report and Written Opinion for International Patent Application No. PCT/US2017/036133, dated Aug. 24, 2017 (10 pages).
International Search Report and Written Opinion for International Patent Application No. PCT/US2018/025206, dated Jul. 3, 2018 (25 pages).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
International Search Report and Written Opinion for International Patent Application No. PCT/US2017/025618, dated Jul. 11, 2017 (22 pages).
Li et al., "Standard reference for the six-minute-walk test in healthy children aged 7 to 16 years," Am J Respir Crit Care Med. 176(2):174-80 (2007).
Park et al., "Ex vivo assessment of contractility, fatigability and alternans in isolated skeletal muscles," J Vis Exp. 69:e4198 (2012) (8 pages).
Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Sugano et al., "Successful gene therapy in utero for lethal murine hypophosphatasia," Hum Gene Ther. 23(4):399-406 (2012).
International Search Report and Written Opinion for International Patent Application No. PCT/US2015/039973, dated Oct. 5, 2015 (12 pages).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
Extended European Search Report for European Application No. 18173111.8, dated Aug. 21, 2018 (9 pages).
"Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8>, (99 pages).
Tomazos et al., "Determination of the Minimal Clinically Important Difference in the Six-Minute Walk Test for Patients with Hypophosphatasia," European Society for Paediatric Endocrinol-

(56) References Cited

OTHER PUBLICATIONS ogy, 55th Annual ESPE, Paris, France, Sep. 10-12, 2016, <http://abstracts.eurospe.org/hrp/0086/hrp0086FC2.5.htm>, (4 pages).
International Search Report and Written Opinion for International Application No. PCT/US18/26868, dated Sep. 7, 2018 (30 pages).

* cited by examiner

FIG. 11

ASFOTASE ALFA SEQ ID NO:1

```
  1 LVPEKEKDPK YWRDQAQETL KYALELQKLN TNVAKNVIMF LGDGMGVSTV
 51 TAARILKGQL HHNPGEETRL EMDKFPFVAL SKTYNTNAQV PDSAGTATAY
101 LCGVKANEGT VGVSAATERS RCNTTQGNEV TSILRWAKDA GKSVGIVTTT
151 RVNHATPSM YAHSADRDWY SDNEMPPEAL SQGCKDIAYQ LMHNIRDIDV
201 IMGGGRKYMY PKNKTDVEYE SDEKARGTRL DGLDLVDTWK SFKPRYKHSH
251 FIWNRTELLT LDPHNVDYLL GLFEPGDMQY ELNRNNVTDP SLSEMVVVAI
301 QILRKNPKGF FLLVEGGRID HGHHEGKAKQ ALHEAVEMDR AIGQAGSLTS
351 SEDTLTVVTA DHSHVFTFGG YTPRGNSIFG LAPMLSDTDK KPFTAILYGN
401 GPGYKVVGGE RENVSMVDYA HNNYQAQSAV PLRHETHGGE DVAVFSKGPM
451 AHLLHGVHEQ NYVPHVMAYA ACIGANLGHC APASSLKDKT HTCPPCPAPE
501 LLGGPSVFLF PPKPKDTLMI SRTPEVTCW VDVSHEDPEV KFNWYVDGVE
551 VHNAKTKPRE EQYNSTYRW SVLTVLHQDW LNGKEYKCKV SNKALPAPIE
601 KTISKAKGQP REPQVYTLPP SREEMTKNQV SLTCLVKGFY PSDIAVEWES
651 NGQPENNYKT TPPVLDSDGS FFLYSKLTVD KSRWQQGNVF SCSVMHEALH
701 NHYTQKSLSL SPGKDIDDDD DDDDDD
```

METHODS OF TREATING A SUBJECT WITH AN ALKALINE PHOSPHATASE DEFICIENCY

This application claims priority to U.S. provisional patent application No. 62/108,689, filed Jan. 28, 2015, the contents of which are hereby incorporated by reference in their entirety.

BACKGROUND

Enzyme replacement therapy (ERT) has been successfully implemented to treat subjects with deficiencies in alkaline phosphatase (AP) activity. In particular, such therapies are useful for treating bone mineralization defects associated with deficient AP activity. Several factors regulate bone formation and resorption, including, for example, serum calcium and phosphate concentrations, and circulating parathyroid hormone (PTH). FGF23, for example, is a hormone that contributes to the regulation of calcium and phosphate homeostasis-promoting renal phosphate excretion and reducing circulating levels of active vitamin D (diminishing intestinal absorption of calcium). ERT treatment that leads to normalized bone formation can potentially have an effect on the production of modulators (e.g., hormones such as, for example, parathyroid hormone (PTH), or vitamin D) that regulate or are regulated by bone mineralization factors (e.g., serum calcium and phosphate).

PTH, also referred to as "parathormone" or "parathyrin," is secreted by the parathyroid gland as an 84-amino acid polypeptide (9.4 kDa). PTH acts to increase the concentration of calcium ($Ca^{2+}$) in the blood by acting upon the parathyroid hormone 1 receptor (high levels of the parathyroid hormone 1 receptor are present in bone and kidney) and the parathyroid hormone 2 receptor (high levels of the parathyroid hormone 2 receptor are present in the central nervous system, pancreas, testes, and placenta).

PTH enhances the release of calcium from the large reservoir contained in the bones by affecting bone resorption by modulation of expression of key genes that regulate bone resorption and formation. Bone resorption is the normal degradation of bone by osteoclasts, which are indirectly stimulated by PTH. Since osteoclasts do not have a receptor for PTH, PTH's effect is indirect, through stimulation of osteoblasts, the cells responsible for creating bone. PTH increases osteoblast expression of the receptor activator of nuclear factor kappa-B ligand (RANKL) and inhibits the expression of osteoprotegerin (OPG). OPG binds to RANKL and blocks it from interacting with RANK, a receptor for RANKL. The binding of RANKL to RANK (facilitated by the decreased amount of OPG available for binding the excess RANKL) stimulates fusion of osteoclasts into multinucleated osteoclasts, ultimately leading to bone resorption. The downregulation of OPG expression thus promotes bone resorption by osteoclasts.

PTH production (synthesis of PTH) is stimulated with high serum levels of phosphates (often present in late stages of chronic kidney disease) by direct effect of serum phosphates on PTH synthesis in the parathyroid gland by promoting the stability of PTH. PTH negatively impacts retention of phosphates in kidneys (promoting loss through urine) affecting homeostasis of phosphates and calcium. The importance of this signaling pathway in the renal response to PTH is highlighted by the renal resistance to PTH associated with deficiency of PTH receptor G protein subunit (Gsalpha) deficiency in patients with pseudohypoparathyroidism. PTH also enhances the uptake of phosphate from the intestine and bones into the blood. In the bone, slightly more calcium than phosphate is released from the breakdown of bone. In the intestines, absorption of both calcium and phosphate is mediated by an increase in activated vitamin D. The absorption of phosphate is not as dependent on vitamin D as is that of calcium. The end result of PTH release from the parathyroid gland is a small net drop in the serum concentration of phosphate.

Secretion of PTH is controlled chiefly by serum $Ca^{2+}$ through negative feedback. Increased levels of calcium reduce PTH secretion, while diminished levels increase PTH secretion. Calcium-sensing receptors located on parathyroid cells are activated when $Ca^{2+}$ is elevated. G-protein coupled calcium receptors bind extracellular calcium and are found on the surface of a wide variety of cells distributed in the brain, heart, skin, stomach, parafollicular cells ("C cells"), and other tissues. In the parathyroid gland, high concentrations of extracellular calcium result in activation of the Gq G-protein coupled cascade through the action of phospholipase C. This hydrolyzes phosphatidylinositol 4,5-bisphosphate (PIP2) to liberate intracellular messengers IP3 and diacylglycerol (DAG). Ultimately, these two messengers result in a release of calcium from intracellular stores and a subsequent flux of extracellular calcium into the cytoplasmic space. The effect of this signaling of high extracellular calcium results in an intracellular calcium concentration that inhibits the secretion of preformed PTH from storage granules in the parathyroid gland. In contrast to the mechanism that most secretory cells use, calcium inhibits vesicle fusion and release of PTH.

Additional mechanisms that affect the amount of PTH available for secretion involve, for example, calcium-sensitive proteases in the storage granules. Upon activation increase the cleavage of PTH (1-84) into carboxyl-terminal fragment, further reducing the amount of intact PTH in storage granules.

PTH also increases the activity of 1-α-hydroxylase enzyme, which converts 25-hydroxycholecalciferol to 1,25-dihydroxycholecalciferol, the active form of vitamin D in kidneys. Vitamin D decreases transcription of the PTH gene. Vitamin D deficiency (often seen in chronic renal disorders) thus causes increases in PTH production. FGF23 is another regulator of parathyroid function, it is secreted by osteocytes or osteoblasts in response to increased oral phosphate intake and other factors. It acts on kidney to reduce expression transporters of phosphates in kidney reducing phosphate retention. In early stages of chronic renal disease, levels of FGF23 are increased to help promote the urinary excretion of phosphates. Elevated FGF23 in chronic renal disorders reduces activity of the Vitamin D 1-α-hydroxylase enzyme and results low production of the active form of vitamin D. In the intestines, absorption of calcium is mediated by an increase in activated vitamin D. Diminished intestinal calcium absorption, which leads to serum hypocalcemia, does not provide strong negative feedback to production/release of PTH from parathyroid gland, causing increased release of PTH from the parathyroid gland. FGF23 appears to directly inhibit PTH secretion as well.

As AP replacement therapy replaces part of a complex pathway, for example, for proper bone formation, there is a need to further characterize the pathway, and to identify analytes that are indicative of therapeutic effects. Such tracking may indicate therapeutic efficacy and/or may identify additional therapies that may become necessary as a result of AP replacement therapy.

SUMMARY

Described herein are methods for treating a subject with an alkaline phosphatase deficiency that comprise monitoring one or more analytes to determine additional therapeutic treatments and procedures.

One aspect of the disclosure is directed to a method of treating a subject with an alkaline phosphatase deficiency, comprising: administering a therapeutically effective amount of an alkaline phosphatase; and monitoring the concentration of one or more bone mineralization analytes, wherein the monitoring the concentration of one or more bone mineralization analytes is indicative for at least one additional treatment regimen for the subject. A non-limiting example for all methods described herein provides that the one or more bone mineralization analytes is at least one analyte selected from the group consisting of: vitamin D, $Ca^{2+}$, and parathyroid hormone. A non-limiting example for all methods described herein provides that the alkaline phosphatase deficiency is hypophosphatasia. A non-limiting example for all methods described herein provides that the alkaline phosphatase is a tissue non-specific alkaline phosphatase, a placental alkaline phosphatase, an intestinal alkaline phosphatase, an engineered alkaline phosphatase, a fusion protein comprising an alkaline phosphatase moiety, or a chimeric alkaline phosphatase. A non-limiting example for all methods described herein provides that the alkaline phosphatase is asfotase alfa (STRENSIQ®) (see, e.g., U.S. Pat. No. 7,763,712; International Pub. No. WO 2005/103263, both herein incorporated by reference in their entirety). A non-limiting example for all methods described herein provides that the bone mineralization analyte is $Ca^{2+}$. A non-limiting example for all methods described herein provides that the subject is determined to be hypocalcemic, the method further comprising treating the subject with a therapeutically effective amount of calcium gluconate, calcium chloride, calcium arginate, vitamin D or a vitamin D analog or parathyroid hormone or a fragment or analog thereof. A non-limiting example for all methods described herein provides that the subject is determined to be hypercalcemic, the method further comprising treating the subject with a therapeutically effective amount of a calcimimetic, a bisphosphonate, prednisone, intravenous fluids, or a diuretic. A non-limiting example for all methods described herein provides that the calcimimetic is cinacalcet. A non-limiting example for all methods described herein provides that the bone mineralization analyte is parathyroid hormone. A non-limiting example for all methods described herein provides that the subject has a statistically significantly low serum concentration of parathyroid hormone, the method further comprising administering a therapeutically effective amount of calcium or vitamin D. A non-limiting example for all methods described herein provides that the subject has a statistically significantly high serum concentration of parathyroid hormone, the method further comprising treating the subject with surgery or by administering a therapeutically effective amount of a calcimimetic, parathyroid hormone or an analog thereof, or a bisphosphonate. A non-limiting example for all methods described herein provides that the calcimimetic is cinacalcet. A non-limiting example for all methods described herein provides that the bone mineralization analyte is vitamin D. A non-limiting example for all methods described herein provides that the subject has a statistically significantly low serum concentration of vitamin D, the method further comprising administering a therapeutically effective amount of vitamin D or an analog thereof.

BRIEF DESCRIPTION OF THE DRAWING(S)

FIG. 1 shows the mean results for serum PTH (Intact pmol/L) over time by disease onset (HPP phenotype) and pooled safety set for all clinical trials (N=71). The time axis shows length of treatment with asfotase alfa in weeks. "Intact" indicates full-length PTH (not the PTH fragment). Bars at each timepoint represent 95% confidence intervals.

FIG. 2 shows mean laboratory test results over time for phosphate (mmol/L). The time axis refers to length of treatment with asfotase alfa in weeks. Bars at each timepoint represent 95% confidence intervals.

FIG. 3 shows mean laboratory test results over time for 25-hydroxyvitamin D (mmol/L). The time axis refers to length of treatment with asfotase alfa in weeks. Bars at each time point represent 95% confidence intervals.

FIG. 4 shows mean results for calcium (mmol/L) over time by disease onset and overall safety set. The time axis refers to length of treatment with asfotase alfa in weeks. Bars at each timepoint represent 95% confidence intervals.

FIG. 5 shows calcium (top panel) and PTH levels (lower panel) with reference ranges for a single patient during treatment with asfotase.

FIG. 6 shows the mean results for serum PTH (Intact, pmol/L) over time through week 312 by disease onset (HPP phenotype) and overall safety set. The time axis shows length of treatment with asfotase alfa in weeks. "Intact" indicates full length PTH (not the PTH fragment). Bars at each timepoint represent 95% confidence intervals.

FIG. 7 shows mean laboratory test results over time through week 312 for phosphate (mmol/L). The time axis refers to length of treatment with asfotase alfa in weeks. Bars at each timepoint represent 95% confidence intervals.

FIG. 8 shows mean laboratory test results over time through week 312 for 25 hydroxyvitamin D (mmol/L). The time axis refers to length of treatment with asfotase alfa in weeks. Bars at each time point represent 95% confidence intervals.

FIG. 9 shows mean results for calcium (mmol/L) over time through week 312 by disease onset and overall safety set. The time axis refers to length of treatment with asfotase alfa in weeks. Bars at each timepoint represent 95% confidence intervals.

FIG. 11 shows the amino acid sequence of asfotase alfa monomer (SEQ ID NO: 1). Asfotase alfa exists as a dimer with inter-subunit disulfide bonds.

DETAILED DESCRIPTION

Figure 1:
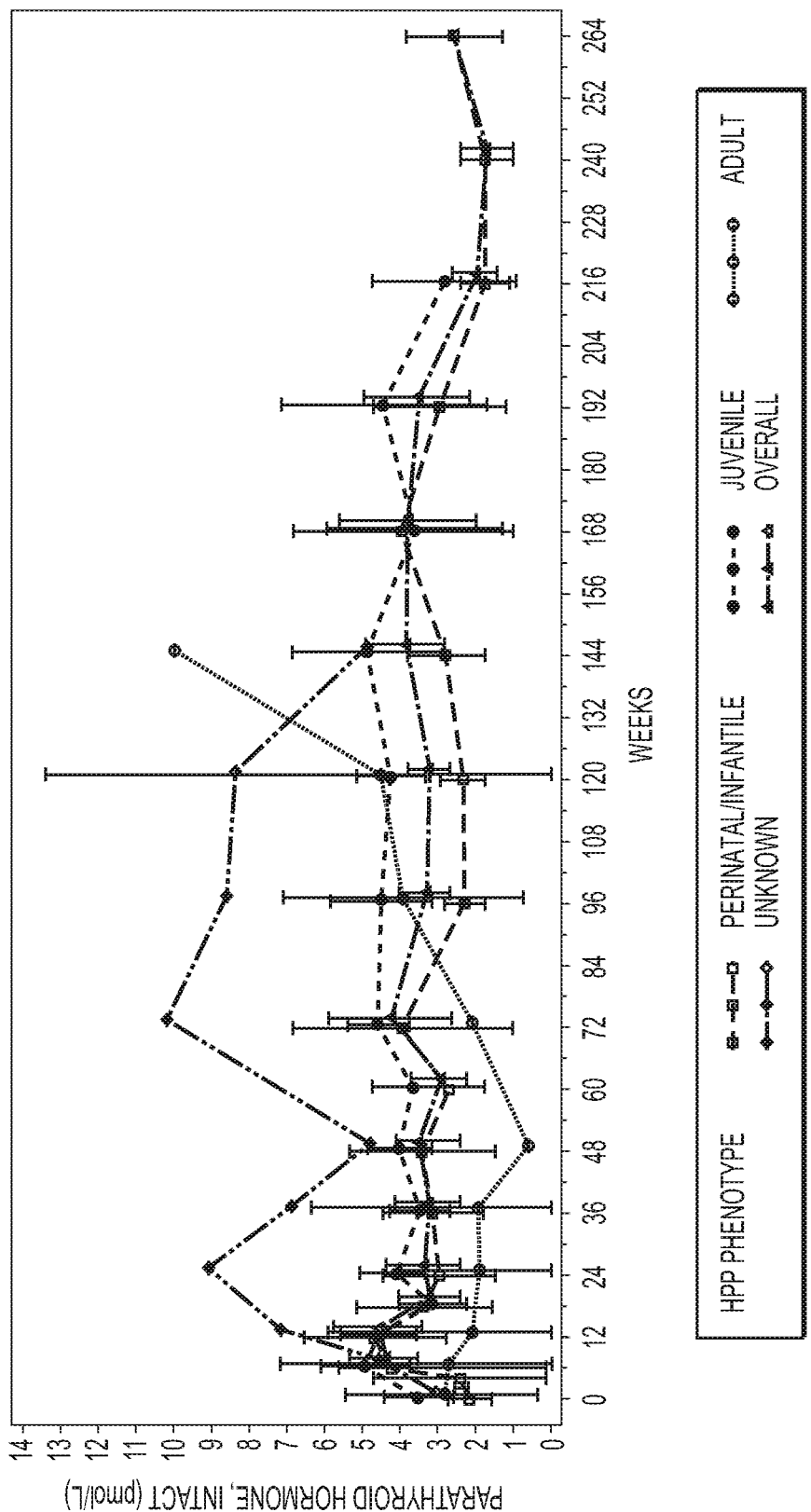

Described herein are materials and methods for monitoring and further treating subjects who are in need of treatment with an alkaline phosphatase or who are being treated with an alkaline phosphatase. The unexpected findings that additional analytes can be monitored to indicate additional treatment regimens led to the materials and methods described herein. Particular analytes can lead to additional treatments, for example, for hypocalcemia, hypercalcemia, osteoporosis, hyperparathyroidism, and vitamin D deficiency.

Various definitions are used throughout this document. Most words have the meaning that would be attributed to those words by one skilled in the art. Words specifically defined either below or elsewhere in this document have the meaning provided in the context of the present disclosure as a whole and as are typically understood by those skilled in the art. For example, as used herein, the singular forms "a," "an," and "the" include plural references unless the content clearly dictates otherwise. Unless otherwise defined, all technical and scientific terms used herein have the same meaning as commonly understood by one of ordinary skill in the art. Methods and materials are described herein for use in the present disclosure; other suitable methods and materials known in the art can also be used. In case of conflict, the present specification, including definitions, will control.

The materials and methods described herein relate to monitoring and further treating subjects who are in need of alkaline phosphatase (AP) replacement therapy or who are undergoing AP replacement therapy. The terms "individual," "subject," "host," and "patient" are used interchangeably and refer to any subject for whom diagnosis, treatment, or therapy is desired, particularly humans. Other subjects may include cattle, dogs, cats, guinea pigs, rabbits, rats, mice, horses and the like. APs are responsible for dephosphorylating a variety of enzymes, and at least one isoform is substantially involved in bone mineralization and formation.

There are at least three APs in humans—intestinal (ALPI), placental (ALPP) and tissue non-specific (TNAP; sometimes referred to as liver/bone/kidney AP or ALPL), in addition to germline AP. TNAP is a membrane-anchored AP that is active extracellularly. Defects in TNAP result in, for example, elevated blood and/or urine levels of three phosphocompound substrates: inorganic pyrophosphate (PPi), phosphoethanolamine (PEA) and pyridoxal-5'-phosphate (PLP) (Whyte, M., *Endocr. Rev.*, 15:439-61, 1994). TNAP is primarily responsible for regulating serum PPi levels (major inhibitor of hydroxyapatite crystal deposition in the bone matrix), and, therefore, is important for bone formation and mineralization. Genetic defects in TNAP, for example, lead to diseases, conditions, or disorders associated with low or decreased bone mineralization symptoms, e.g., hypophosphatasia (HPP).

Defects in TNAP activity can lead to a variety of diseases, disorders, and symptoms. Hypophosphatasia (HPP), for example, is a rare, heritable form of rickets or osteomalacia (Whyte, M. "Hypophosphatasia," *In The Metabolic and Molecular Bases of Disease*, 8$^{th}$ ed., 5313-29, Eds C. Scriver, A. Beaudet, W. Sly, D. Valle & B. Vogelstein. New York: McGraw-Hill Book Company, 2001). HPP is caused by loss-of-function mutation(s) in the gene (ALPL) that encodes TNAP (Weiss, M. et al., *Proc. Natl. Acad. Sci. USA*, 85:7666-9, 1988; Henthorn, P. et al., *Proc. Natl. Acad. Sci. USA*, 89:9924-8, 1992; Henthorn, P. & Whyte, M., *Clin. Chem.*, 38:2501-5, 1992; Zurutuza, L. et al., *Hum. Mol. Genet.*, 8:1039-46, 1999). The biochemical hallmark is subnormal AP activity in serum (hypophosphatasemia).

HPP is an ultra-rare genetic disorder whereby TNAP activity is either absent or barely detectable in affected patients. While differences in patterns of inheritance and mutations cause variability in age at symptom onset and disease severity, all HPP patients share the same primary pathophysiological defect, the failure to mineralize bone matrix (resulting in rickets or osteomalacia) due to lack of TNAP. This primary defect in infants and children, alone or in combination with associated metabolic disturbances, can lead to deformity of bones, impaired growth, and decreased motor performance. This primary pathophysiological mechanism can rapidly lead to progressive damage to multiple vital organs, seizures due to a CNS deficiency in functional vitamin B6, and developmental delays. Subjects with HPP, left untreated, can develop, for example, hypercalcemia, and hyperphosphatemia.

All forms of HPP share the same underlying genetic and biochemical defect; however, the diagnosis of HPP actually encompasses a spectrum of disease. Published classifications of HPP have historically taken into account the age at which clinical manifestation(s) first appear, dividing the disease into the following categories: perinatal (onset in utero and at birth), infantile (onset post-natal to 6 months of age), juvenile (also described as childhood, onset from 6 months to 18 years), and adult (onset after 18 years of age). Other milder forms of the disease, including benign perinatal HPP and odontohypophosphatasia, have also been described.

HPP manifest in utero and may cause stillbirth. At the time of delivery, limbs may be shortened and deformed from profound skeletal hypomineralization, and radiographic examination often reveals an almost total absence of bony structures. Most patients with perinatal HPP have life-threatening disease, and death generally results from respiratory insufficiency due to pulmonary hypoplasia and poor functioning due to a rachitic chest. Patients with infantile-onset HPP often appear normal at birth but typically present with skeletal abnormalities and failure to thrive within the first six months life. These patients can have a flail chest from rachitic deformity of the thorax; and, together with rib fractures, this may predispose them to pneumonia and respiratory compromise. Mortality, usually due to pulmonary complications, has been reported to be as high as 50% (Whyte M. Hypophosphatasia. In: Glorieux F H, Pettifor J M, Juppner H, editors. Pediatric Bone: Biology and Diseases. London, UK, Academic Press; 2012: pp. 771-94; Caswell A. et al., *Crit. Rev. Clin. Lab. Sci.*, 28:175-232, 1991). Other clinical features may include, for example, functional craniosynostosis with resultant increased intracranial pressure and papilledema, and non-traumatic fractures. Hypercalcemia and hypercalciuria are also common, and nephrocalcinosis with renal compromise may occur. Weakness and delayed motor development are also common complications of infantile-onset HPP and seizures may occur secondary to vitamin B6 deficiency in the central nervous system.

In juvenile-onset patients, radiographs of the long bones often reveal focal bony defects that project from the growth plates into the metaphyses, sometimes described as "tongues" of radiolucency. Physeal widening, irregularities of the provisional zones of calcification, and metaphyseal flaring with areas of radiolucency adjacent to areas of osteosclerosis may also be present. Premature bony fusion of cranial sutures has also been observed in some patients, leading to potential increased intracranial pressure, proptosis, and cerebral damage. Rachitic deformities, including, for example, beading of the costochondral junctions, either bowed legs or knock-knees, and enlargement of the wrists, knees, and ankles from flared metaphyses, are common, and often result in short stature. Walking is frequently delayed, and a nonprogressive myopathy characterized by limb weakness, especially of the proximal muscles of the lower extremities, has also been described (Seshia, S. et al., *Arch. Dis. Child.*, 65:130-1, 1990). Skeletal pain and stiffness may also be present and non-traumatic fractures are common. Nephrocalcinosis may develop in juvenile-onset HPP as well.

First signs of HPP may also present later in life (as in the adult form of HPP); however, upon questioning, many adult patients report a history of early tooth loss or rickets during childhood. In adult HPP, hypomineralization manifests as osteomalacia. Adult HPP patients are subject to recurrent, poorly healing fractures, often in the metatarsals and/or femur. Complaints of pain in the thighs and hips from subtrochanteric femoral pseudofractures are also common. Radiographs often reveal the presence of osteopenia and chondrocalcinosis. In some patients, deposition of calcium pyrophosphate dehydrate occurs, leading to PPi arthropathy. Although adult HPP has been described as 'mild', manifestations of the disease in adults can be severe and debilitating, often requiring multiple surgeries and the use of supportive devices to perform activities of daily living.

Subjects with a defect in an endogenous AP, e.g., TNAP, are in need if AP enzyme replacement therapy (ERT). AP-ERT has been successful, for example, in treating HPP. ERT replaces an enzyme in subjects in whom that particular enzyme is deficient or absent. ERT does not affect the underlying genetic defect, but increases the concentration of enzyme in which the patient is deficient. The copy of the enzyme to be replaced, for example, can be a copy of the endogenous enzyme, an isoform of the enzyme, an ortholog of the enzyme, a chimeric version of the enzyme, a fusion protein with the relevant active site of the enzyme or an otherwise engineered version of the enzyme. ERT can be accomplished, for example, by providing the enzyme itself or by causing the enzyme to be expressed in particular tissues or cells of the subject (e.g., through gene therapy methods, mRNA methods, transcriptional or translational activation methods, etc.).

Asfotase alfa or STRENSIQ®, for example, is a dimeric fusion protein that comprises two monomers with a TNAP phosphatase domain fused to an Fc chain and a bone tag to target the molecule to bone. The APs described herein can be, for example, intact native proteins, modified proteins or fusion proteins. Fusion proteins can comprise, for example, sequences to stabilize the protein, increase residence time in a patient, and/or target the fusion protein to a particular tissue, e.g., bone. Fusion proteins, for example, can comprise Fc domains or albumin moieties. Bone tags are typically negatively charged regions, e.g., poly-aspartate or poly-glutamate sequences, e.g., between about 5 to about 50, between about 10 to about 25, between about 67 to about 30, about 5, about 10, about 15, about 20, about 25, about 30, about 35, about 40, about 45, about 50 or more aspartates, glutamates, or other negatively charged amino acids (natural or non-naturally occurring).

As described herein, treatment of a subject with AP-ERT can result in, for example, hypocalcemia, hyperparathyroidism, hypophosphatemia, vitamin D deficiency, and/or symptoms or side effects thereof. Such situations can occur, for example, in cases where the mineral defect is profound and availability of calcium and phosphorous for formation of hydroxyapatite is not adequate (e.g., not enough supplementation in food, not enough utilization of the minerals available in the food or profound loss through urine). Treatment of one or more of these effects can lead to "overcorrection" of the effect, and, therefore, require additional treatment to reverse the overcorrection. As described herein, monitoring of calcium, PTH, phosphate and vitamin D, therefore, can improve the treatment of a subject in need of or being treated with AP-ERT.

Described herein are also materials and methods for identifying subjects who, prior to or at the time of treatment, for example, AP-ERT, need to undergo treatment to normalize one or more metabolites associated with bone mineralization (e.g., PTH, $Ca^{2+}$, vitamin D, and/or phosphate). A subject in need of AP-ERT, for example, who is hypocalcemic prior to AP-ERT treatment, would benefit from having normalized calcium levels prior to AP-ERT treatment.

Routine urinalysis and serum hematology and chemistries, for example, can be obtained before, during and after treatment using AP-ERT (e.g., treatment with asfotase alfa). Calcium and phosphate metabolism should be monitored periodically with measurements of serum calcium, phosphate and PTH levels and urinary calcium excretion. Dietary intake of calcium should be adjusted according to PTH levels and urinary calcium levels (ionized and adjusted for other markers, e.g., creatinine or albumin). When using asfotase alfa in patients with hypomineralization, e.g., with HPP rickets or osteomalacia, it is useful to monitor calcium concentration closely, as rapid intake of calcium into the bone matrix can result in episodes of hypocalcemia. In certain examples, this is particularly relevant during the initial month or months of treatment. To prevent sequelae of hypocalcemia, including potential hypocalcemia-induced seizures, supplementation of calcium, or treatment with calcimimetics, for example, can be useful for those patients whose calcium levels are statistically significantly low or high.

As used herein, an "engineered" molecule is one that can be isolated from natural sources, synthesized and/or modified chemically. If the engineered molecule is a biological molecule, an engineered molecule can be one that is mutagenized, fused to a second molecule, e.g., forming a fusion protein, attached to a specific functional moiety, e.g., a targeting domain, purification domain, active site, etc., humanized, or made into a chimeric protein by switching particular domains with other proteins or isoforms. The engineering is the process of modifying the molecule in a particular manner to achieve a desirable result.

As used herein, "fusion protein" refers to an engineered protein that comprises residues of moieties from two or more different proteins. Fusion genes, which can be used to generate fusion proteins, are created through the joining of two or more coding sequences that code for separate proteins. Translation of a fusion gene results in a single or multiple polypeptides with functional properties derived from each of the original proteins. Recombinant fusion proteins are created by recombinant DNA technology.

As used herein, "chimeric proteins" are proteins that comprise moieties from at least two distinct proteins. The term refers to hybrid proteins made of polypeptides having different functions or physicochemical patterns.

The subjects described herein have an AP activity defect. Such a defect can arise, for example, due to a genetic anomaly (e.g., a mutation) that causes the AP enzyme to not be produced or to be produced in an inactive form. Although such a defect can occur in any of the AP isoforms, of particular interest for the present disclosure are AP defects that lead to bone mineralization defects, e.g., HPP.

Described herein are findings indicating that patients who are in need of or who are undergoing treatment, e.g., ERT-AP treatment, for a bone mineralization disease, disorder, condition or symptoms thereof, e.g., HPP, can be monitored for one or more analytes that are indicative of the need for additional treatments or a need to alter the current treatment regimen, e.g., alter the dosage and/or frequency of dosage.

"Treatment" refers to the administration of a therapeutic agent or the performance of medical procedures with respect to a patient or subject, for any of prophylaxis (prevention), cure, or reduction of the symptoms of the disease, disorder, condition, or symptoms from which the subject suffers.

The treatments (therapies) described herein can also be part of "combination therapies." Combination therapy can be achieved by administering two or more agents, each of which is formulated and administered separately, or by administering two or more agents in a single formulation. One active ingredient can be, for example, useful for treating, for example, a disease, disorder, condition or symptoms associated with a TNAP defect, e.g., hypophosphatasemia, or symptoms associated with treatment by the active agent ("side effects"). Other combinations are also encompassed by combination therapy. For example, two or more agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days or weeks. Thus, the two or more agents can be administered within minutes of each other or within any number of hours of each other or within any number or days or weeks of each other.

As used herein, a "therapeutically effective dosage" or "therapeutically effective amount" results in a decrease in severity of disease, disorder, condition or symptoms thereof (e.g., associated with aberrant AP activity, e.g., HPP), an increase in frequency and duration of disease symptom-free periods, or a prevention of impairment or disability due to the disease affliction.

As described herein, treatment with AP replacement therapy is more effective or leads to overall improved health or quality of life, when the treated subject is further monitored for one or more additional analytes. PTH, calcium ($Ca^{2+}$), phosphate and vitamin D concentrations can each be monitored or individually monitored during AP-ERT, and the specific concentrations are indicative of, for example, efficacy of treatment and/or the need for one or more additional therapeutic regimen(s).

PTH acts on osteoblasts in bone and tubular cells within the kidney via G-protein-linked receptors that stimulate adenylate cyclase production of cyclic AMP. In bone, within one or two hours, PTH stimulates a process known as osteolysis in which calcium in the minute fluid-filled channels (canaliculi/lacunae) is taken up by syncytial processes of osteocytes and transferred to the external surface of the bone and, hence, into the extracellular fluid. Some hours later, it also stimulates resorption of mineralized bone; a process that releases both $Ca^{2+}$ and phosphate into the extracellular fluid.

Monitoring PTH concentration in a sample obtained from a subject, for example, is of interest for better treating the subject, as AP-ERT can have an effect on PTH concentration. A determination that the treated subject's serum PTH concentration is statistically significantly lower or higher than normal, for example, can lead to revised treatment plans (e.g., combining the AP-ERT plan with one or more therapeutic agents for treating, for example, hyperparathyroidism, e.g., with cinacalcet). In cases where PTH concentration is determined to be statistically significantly high, e.g., hyperparathyroidism, the subject can be treated with higher levels of the AP-ERT, e.g., asfotase alfa, to reduce PTH levels in the case where a patient does not show good response in term of bone mineralization to initial dose.

As used herein, the term "sample" refers to biological material from a subject. Although serum concentration is of interest, samples can be derived from many biological sources, including, for example, single cells, multiple cells, tissues, tumors, biological fluids, brain extracellular fluid, biological molecules or supernatants or extracts of any of the foregoing. Examples include tissue removed for biopsy, tissue removed during resection, blood, urine, lymph tissue, lymph fluid, cerebrospinal fluid, amniotic fluid, mucous and stool samples. The sample used will vary based on the assay format, the detection method and the nature of the tumors, tissues, fluids, cells or extracts to be assayed. Methods for preparing samples are known in the art and can be readily adapted to obtain a sample that is compatible with the method utilized.

As used herein, "statistical significance" is a statistical term that informs as to the certainty that a difference or relationship exists, e.g., that a sample value id statistically significantly different from a normal or baseline value. It is conferred by finding a low probability of obtaining at least as extreme results given that the null hypothesis is true. It is an integral part of statistical hypothesis testing where it determines whether a null hypothesis can be rejected. In any experiment or observation that involves drawing a sample from a population, there is the possibility that an observed effect would have occurred due to sampling error alone. But if the probability of obtaining at least as extreme result (large difference between two or more sample means), given the null hypothesis is true, is less than a pre-determined threshold (e.g., 5% chance), then an investigator can conclude that the observed effect actually reflects the characteristics of the population rather than just sampling error. A test for statistical significance involves comparing a test value to some critical value for the statistic. The procedure to test for significance is the same—decide on the critical alpha level (i.e., the acceptable error rate), calculate the statistic and compare the statistic to a critical value obtained from a table. P-values, the probability of obtaining the observed sample results (or a more extreme result) when the null hypothesis is actually true, are often coupled to a significance or alpha ($\alpha$) level, which is also set ahead of time, usually at about 0.05 (5%). Thus, if a p-value was found to be less than about 0.05, then the result would be considered statistically significant and the null hypothesis would be rejected. Other significance levels, such as about 0.1, about 0.075, about 0.025 or about 0.01 can also be used. As used herein, a "statistically significantly low" concentration of an analyte is one that is lower than the normal or baseline situation for a control, e.g., healthy, subject. Conversely, a "statistically significantly high" concentration of an analyte is one that is higher than the normal or baseline concentration of the analyte for a control subject.

PTH promotes osteoclast function and leads to bone resorption, thereby increasing serum $Ca^{2+}$ and phosphate concentrations. Low levels of serum $Ca^{2+}$ fail to exhibit negative feedback effect on the release or production of PTH from the thyroid, whereas high concentrations of serum $Ca^{2+}$, by exhibiting a negative feedback effect on release and/or production of PTH, lead to decreased PTH levels in blood. In a related pathway, vitamin D increases adsorption of $Ca^{2+}$ and phosphate in the intestine, leading to elevated levels of serum $Ca^{2+}$ and, therefore, lower bone resorption. Effects of active vitamin D (1, 25 $(OH)_2D$) on bone, however, are diverse and can affect formation or resorption.

Although, hypoparathyroidism (hypoPT) is one of the few major hormone deficiency diseases that is often not treated with the missing hormone, hormone replacement therapies are available. Bovine PTH has been purified and used as experimental treatment, however utility as a treatment was diminished, mainly because of antibody formation and costs.

Approval of fully humanized truncated PTH (Teriparatide, PTH (1-34)) and intact parathyroid hormone (Preotact, PTH (1-84)) for treatment of osteoporosis, has made the PTH drugs more accessible and thereby made clinical trials with PTH treatment of hypoPT feasible. Patients with hypoPT experience an improved quality of life when treated with PTH compared with conventional treatment with 1α-hydroxylated vitamin D metabolites and calcium supplements, although hypoPT is still treated, for example, by supplementing calcium and/or vitamin D.

Primary hyperparathyroidism results from a hyperfunction of the parathyroid glands. Over secretion of PTH can be due, for example, to a parathyroid adenoma, parathyroid hyperplasia or a parathyroid carcinoma. This disease is often characterized by the presence of kidney stones, hypercalcemia, constipation, peptic ulcers and depression.

Secondary hyperparathyroidism is due to physiological secretion of PTH by the parathyroid glands in response to hypocalcemia (low blood calcium levels). The most common causes are vitamin D deficiency and chronic renal failure. Lack of vitamin D leads to reduced calcium absorption by the intestine leading to hypocalcemia and increased PTH secretion. This increases bone resorption. In chronic renal failure the problem is more specifically failure to convert vitamin D to its active form in the kidney. The bone disease in secondary hyperparathyroidism caused by renal failure is termed renal osteodystrophy.

Tertiary hyperparathyroidism is seen in patients with long-term secondary hyperparathyroidism, which eventually leads to hyperplasia of the parathyroid glands and a loss of response to serum calcium levels.

Quaternary and quintary hyperparathyroidism are rare conditions that may be observed after surgical removal of primary hyperparathyroidism, when it has led to renal damage that now again causes a form of secondary (quaternary) hyperparathyroidism that may itself result in autonomy (quintary) hyperparathyroidism. Additionally, quaternary hyperparathyroidism may ensue from hungry bone syndrome after parathyroidectomy.

Primary hyperparathyroidism can be treated, for example, by surgery (parathyroidectomy) if treatment, for example, with calcimimetics is unsuccessful. Secondary hyperparathyroidism can be treated, for example, by vitamin D supplementation and/or by the use of calcimimetics (e.g., cinacalcet). Other forms of hyperparathyroidism are variations of secondary hyperparathyroidism, and treatments involve approaches similar to those used for primary and secondary hyperparathyroidism.

Low plasma calcium stimulates PTH release (by negating the inhibition of PTH release), and PTH acts to resorb $Ca^{2+}$ from the pool in bone and to enhance renal re-absorption of $Ca^{2+}$. High plasma calcium stimulates calcitonin secretion, which lowers plasma calcium by inhibiting bone resorption.

Normal blood calcium level is between about 8.5 to about 10.5 mg/dL (2.12 to 2.62 mmol/L; some reports use the values of between about 8.0 to about 10.0 mg/dL) and that of ionized calcium is 4.65 to 5.25 mg/dL (1.16 to 1.31 mmol/L). Hypocalcemia or hypercalcemia is characterized by a statistically significantly low or high serum calcium concentration. Hypocalcemic subjects, for example, typically display a serum calcium concentration of about 2.5 mg/dL or lower (Sorell, M. & Rosen, J., *J. Pediatr.*, 87:67-70, 1975). A hypocalcemic subject, for example, can have serum calcium concentration of about 7.0 mg/dL or lower, about 5.0 mg/dL or lower, about 1.0 mg/dL or lower, or about 0.5 mg/dL or lower.

Common causes of hypocalcemia include hypoparathyroidism, vitamin D deficiency and chronic kidney disease. Symptoms of hypocalcemia include, for example, neuromuscular irritability (including tetany as manifested by Chvostek's sign or Trousseau's sign, bronchospasm), electrocardiographic changes and seizures. Treatment options include, for example, supplementation of calcium and some form of vitamin D or its analogues, alone or in combination. Intravenous calcium gluconate 10% can be administered, or if the hypocalcemia is severe, calcium chloride can be given. Other treatments involve multivitamin supplementation, in oral, chewable, or liquid forms.

Hypercalcemia is an elevated $Ca^{2+}$ level in the blood, which is often indicative of other disease(s). It can be due to excessive skeletal calcium release, increased intestinal calcium absorption or decreased renal calcium excretion. The neuromuscular symptoms of hypercalcemia are caused by a negative bathmotropic effect due to the increased interaction of calcium with sodium channels. Since calcium blocks sodium channels and inhibits depolarization of nerve and muscle fibers, increased calcium raises the threshold for depolarization. Symptoms of hypercalcemia include, for example, renal or biliary stones, bone mineralization defects and bone pain, abdominal pain, nausea, vomiting, polyuria depression, anxiety, cognitive dysfunction, insomnia, coma, fatigue, anorexia and pancreatitis. Hypercalcemia is defined as a serum calcium level greater than about 10.5 mg/dL (>2.5 mmol/L). Hypercalcemia can also be classified based on total serum and ionized calcium levels, as follows: Mild: total calcium 10.5-11.9 mg/dL (2.5-3 mmol/L) or ionized calcium 5.6-8 mg/dL (1.4-2 mmol/L); Moderate: total calcium 12-13.9 mg/dL (3-3.5 mmol/L) or ionized calcium 5.6-8 mg/dL (2-2.5 mmol/L); Hypercalcemic crisis: total calcium: >14-16 mg/dL (3.5-4 mmol/L) or ionized calcium 10-12 mg/dL (2.5-3 mmol/L).

Hypercalcemia is treated a number of ways, including, for example, using fluids and diuretics for an initial therapy (hydration, increasing salt intake, and forced diuresis). Diuretic treatments include, for example, furosemide, and they can be given to permit continued large volume intravenous salt and water replacement while minimizing the risk of blood volume overload and pulmonary edema. In addition, loop diuretics tend to depress renal calcium reabsorption thereby helping to lower blood calcium levels. Caution must be taken to prevent potassium or magnesium depletion. Additional therapies include, for example, bisphosphonates, plicamycin, gallium nitrate, glucocorticoids and calcitonin. Bisphosphonates are pyrophosphate analogues with high affinity for bone, especially areas of high bone turnover. They are taken up by osteoclasts and inhibit osteoclastic bone resorption. Available drugs include, for example, etidronate, tiludronate, IV pamidronate, alendronate, zoledronate, and risedronate. Calcitonin blocks bone resorption and also increases urinary calcium excretion by inhibiting renal calcium reabsorption. Phosphate therapy can correct the hypophosphatemia in the face of hypercalcemia and lower serum calcium. Calcium mimetics, e.g., cinacalcet, are also used to lower serum calcium concentrations.

Hypovitaminosis D is a deficiency of vitamin D. It can result from inadequate nutritional intake of vitamin D coupled with inadequate sunlight exposure (in particular sunlight with adequate ultraviolet B rays), disorders that limit vitamin D absorption, and conditions that impair the conversion of vitamin D into active metabolites including certain liver, kidney, and hereditary disorders. Deficiency results in impaired bone mineralization and leads to bone softening diseases including rickets in children and osteomalacia and osteoporosis in adults. Maintenance doses of both calcium and vitamin D are often necessary to prevent further decline.

EXEMPLIFICATION

The following examples do not limit the scope of the invention as disclosed and described in the claims.

Example 1. PTH and Calcium

When evaluating results by age at disease onset, mean and median PTH levels were notably higher in patients with infantile- and juvenile-onset HPP during the first 12 weeks of treatment compared with later time points, and were likely associated with the bone mineralization process and the monitoring thereof. In some cases, multivitamins, calcium, vitamin D, vitamin A, vitamin K, cinacalcet, pyridoxal phosphate calcium, and/or calcitonin were administered to patients in order to normalize PTH, calcium, and phosphate levels concomitantly with the monitoring process.

Mean PTH levels in patients with adult-onset HPP tended to be lower than those observed in the infantile- and juvenile-onset HPP patients through approximately Week 72. These comparisons, however, involved only two patients with adult-onset HPP. FIG. 1 provides the change in serum PTH over time in the clinical studies.

Patients were subdivided by Baseline PTH level, and the details of the changes in the initial period after the start of asfotase alfa treatment are as follows:

For the nine patients with low PTH at Baseline:
Seven patients with normal calcium levels at Baseline and lower calcium levels post-treatment had a rise in PTH. All except one patient showed radiological improvements, as determined by the RSS score (scoring of rickets).
One patient, who had high Baseline serum calcium, showed no change in serum calcium levels and no change in PTH by Week 6, at which time the patient was discontinued from the study. Note that this patient received only two doses of asfotase alfa and was subsequently withdrawn; therefore, no change in calcium or PTH was expected.
One patient with a high Baseline serum calcium level had normalization of serum calcium by Week 24. PTH data beyond Week 6 is not available for this patient (at Week 6, PTH was unchanged). This patient showed no improvements in rickets at Week 12 (7 weeks after asfotase alfa dose was increased), however showed a decrease in RSS score by Week 24.
For the 13 Patients with Normal PTH at Baseline:
12 patients with normal PTH and normal calcium levels at Baseline responded with small or no change in serum calcium levels and no or slight change in PTH levels. All except 1 patient showed radiographic improvement.
One patient with calcium levels at the upper limit of normal at Baseline responded with normalization of calcium levels and large increase in PTH. This patient showed radiographic improvement.
Only one patient had high PTH at Baseline with normal calcium levels. The patient responded with lowering of serum calcium levels and large rise in PTH levels. This patient did not show radiological improvement during the periods of rise in PTH.
One patient had no available Baseline PTH results, but the earliest result at Week 6 showed values in the normal range. Calcium remained within normal ranges with some oscillation until Week 60. The patient showed worsening of rickets (RGI-C score at Week 12 was negative; −1.67) and growth scores on the initial dose of asfotase alfa of 6 mg/kg/week. After the dose was increased to 9 mg/kg/week due to continued worsening of growth delays, the patient showed improvement in radiographic signs (at Week 36, RSS score improved 4.5 points since week 24 assessment) and PTH increased above the normal range. PTH further increased more steeply until it peaked at Week 72. Note that calcium levels showed a drop at Week 48 (although were still within the normal limits) and then fell below normal at Week 60, however rebounded to normal at Week 72. In this patient, low vitamin D levels and low urine calcium/creatinine ratios were found coincident with the observed elevation of PTH level.

Example 2. Phosphate

Mean serum phosphate values tended to be variable through Week 24 in all HPP onset categories, and then appeared to normalize and stabilize with continued treatment. Some decreases in serum phosphate levels appeared to coincide with decreases in serum calcium levels during the first several weeks of treatment, which likely was due to the intense bone mineralization processes that occurred early in treatment.

Figure 2:
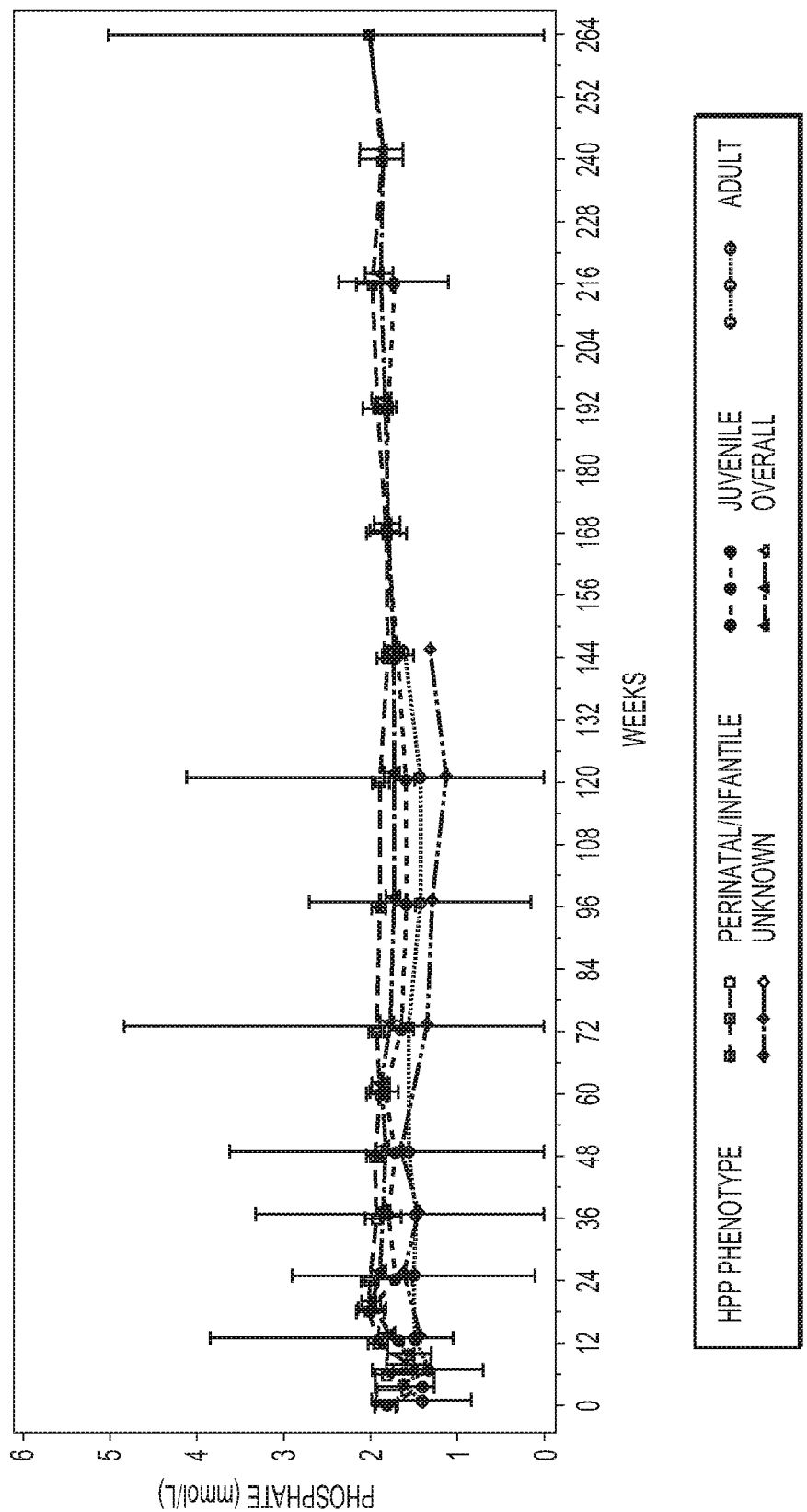

Three patients (infantile-onset) had a shift from normal values for phosphate at Baseline to low values during treatment, and 21 patients (15 infantile-onset; 5 juvenile-onset; 1 adult-onset) with low or normal values at Baseline had a shift to high values during treatment; at the last visit, no patients had shifted from normal or high values to low values, and 5 patients (infantile-onset) had shifted from normal values to high values; see FIG. 2.

Example 3. Vitamin D

Figure 3:
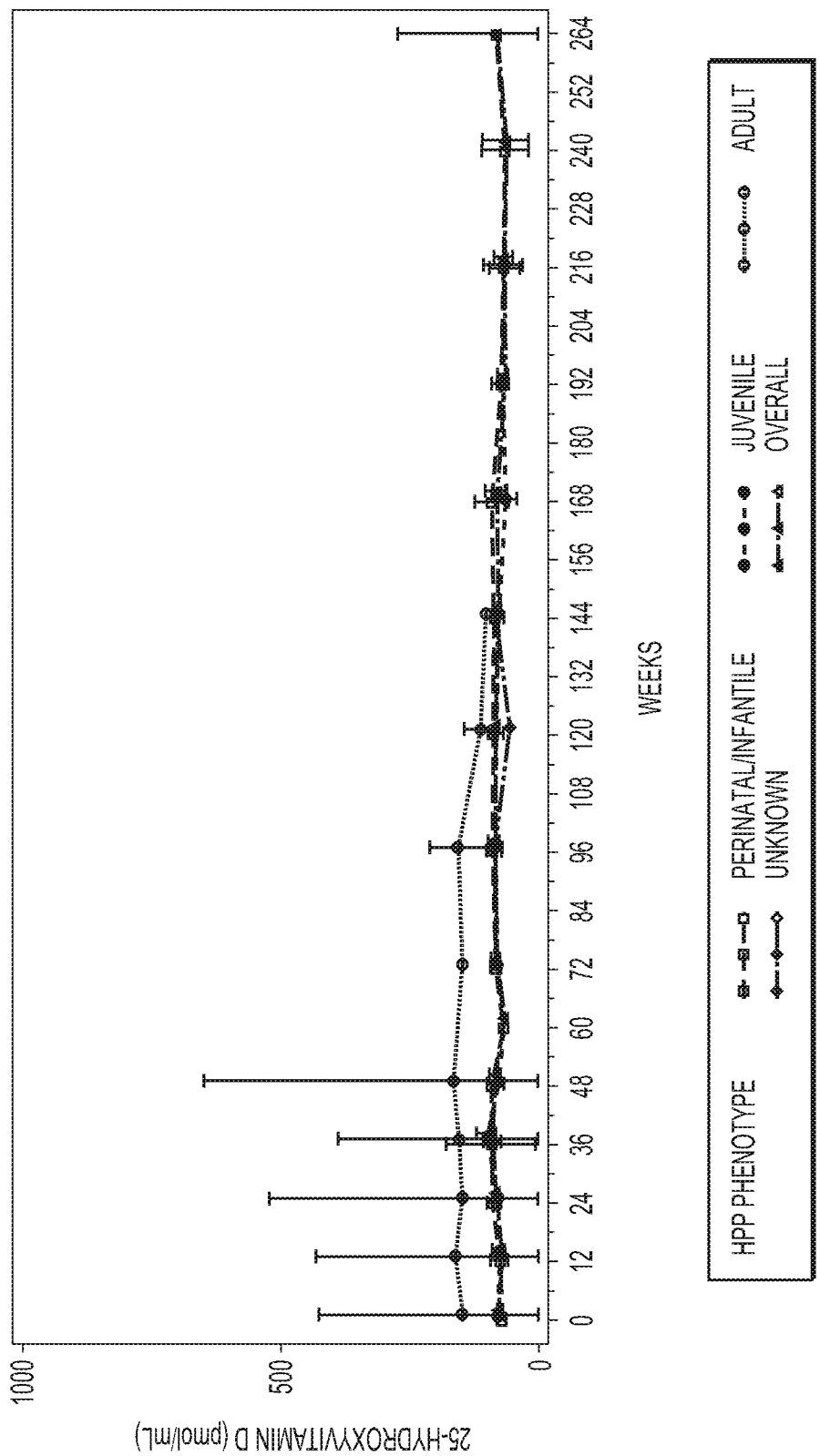

Mean 25-OH vitamin D values were consistently higher in patients with adult-onset HPP than in patients in the other HPP onset categories; however, these values did decrease slightly over time, and there were only 2 patients with adult-onset HPP included in the study. Mean and median 25-OH vitamin D values in the other HPP onset categories were relatively consistent over time; see FIG. 3. In patients where vitamin D values were monitored and identified as deficient or lower than desired by the clinician (i.e., less than 20 ng/ml), vitamin D was supplemented with vitamin D in the form of an oral medication, i.e., as children's vitamins, adult multivitamins, or vitamin D capsules. Vitamin D in some cases was administered as an intramuscular injection or in combination dosages with calcium, vitamin A, and/or vitamin K. Calcitriol, cholecalciferol, and/or ergocalciferol were also administered as needed.

Example 4

Systematic analyses of pre- and post-treatment serum calcium, parathyroid hormone (PTH), phosphate and vitamin D were performed.

Figure 4:
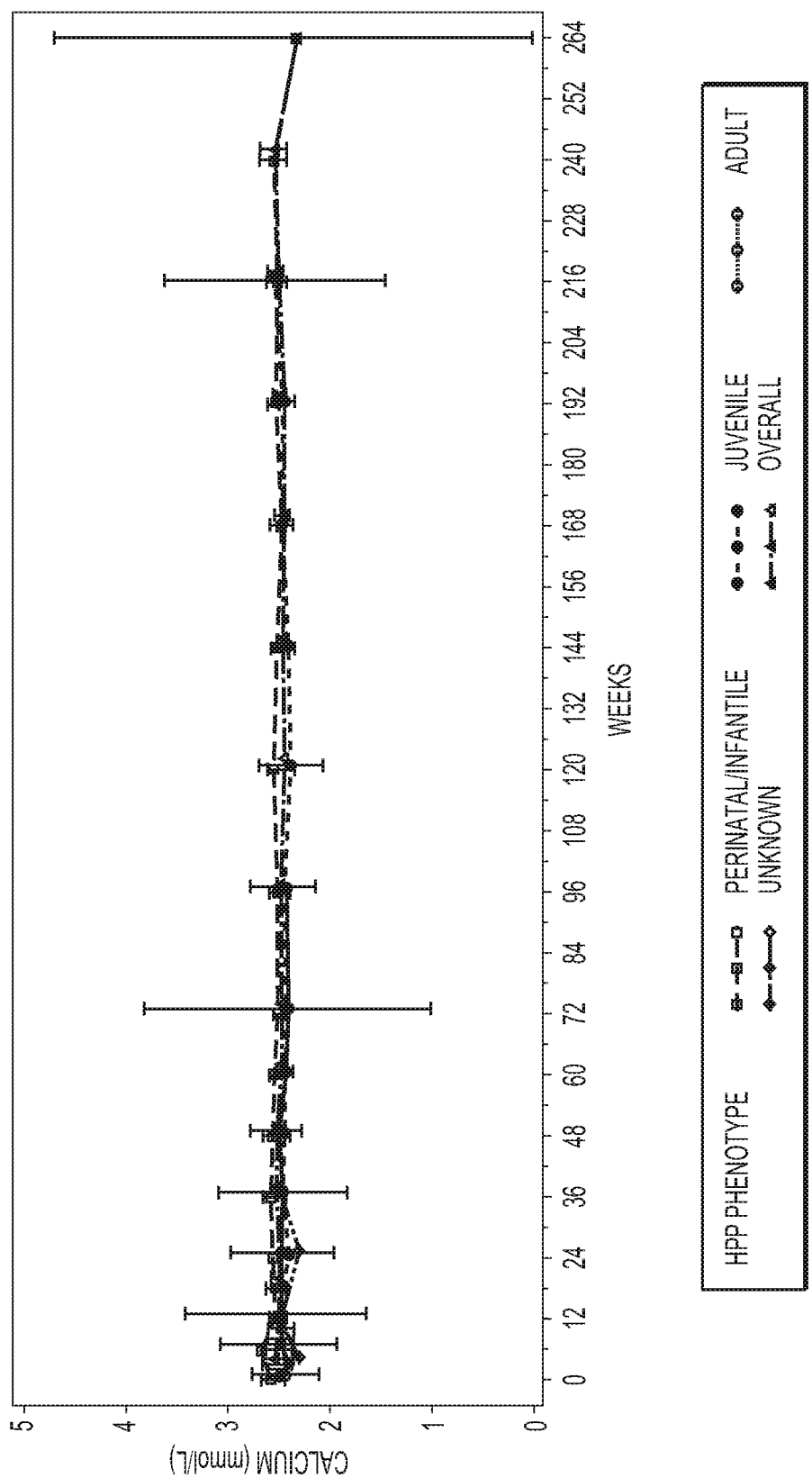

Calcium: serum calcium levels were variable at Baseline, ranging from 1.92 to 4.03 mmol/L. Although the changes in mean and median calcium levels over the course of treatment with asfotase alfa were not remarkable, levels tended to stabilize and become less variable; calcium levels ranged from 1.82 to 2.80 mmol/L at Week 24, and from 2.12 to 3.67 mmol/L at the last visit, basically eliminating the episodes of hypocalcemia and the range of hypercalcemia was lowered to nearly normal (i.e., upper range is 3.5 mmol/L). Increases in calcium above the normal range were generally small and, when present, were most notable at Baseline and tended to normalize over the course of asfotase alfa treatment with the increased calcium deposition in the bone as noted on X-ray. When evaluating results by age at disease onset, the small increases in calcium were generally seen in patients with infantile-onset HPP, and calcium levels in these patients tended to normalize during treatment (Table 1 and FIG. 4).

Parathyroid Hormone: mean and median PTH levels increased with treatment, most notably during the first 12 weeks of treatment with asfotase alfa. This increase was likely due to a physiologic response secondary to increases in the bone mineralization process associated with asfotase alfa treatment. The variability in PTH levels noted at Baseline and throughout treatment may be due to factors that affect PTH levels, including, but not limited to: age, body mass index (BMI), serum creatinine levels, serum calcium levels and vitamin D levels. When evaluating results by age at disease onset, mean and median PTH levels were notably higher in patients with infantile- and juvenile-onset HPP during the first 12 weeks of treatment compared with later time points, and were likely associated with the bone mineralization process. Mean PTH levels in patients with adult-onset HPP tended to be lower than those observed in the infantile- and juvenile-onset HPP patients through approximately Week 72; there are several variables that can affect PTH levels (Table 1 and FIG. 1).

Phosphate: mean serum phosphate values were variable through Week 24 in patients with infantile-, juvenile- and adult-onset HPP, and then appeared to normalize and stabilize with continued treatment with asfotase alfa. Some decreases in serum phosphate levels appeared to coincide with decreases in serum calcium levels during the first several weeks of treatment, which were likely due to the intense bone mineralization processes occurring early in treatment (Table 1 and FIG. 2).

Vitamin D: changes over time for vitamin D were not clinically meaningful; some of the variability seen in vitamin D results may be reflective of concomitant vitamin D supplements taken by some patients. When evaluating results by age at disease onset, mean vitamin D values were consistently higher in patients with adult-onset HPP than in patients with infantile- or juvenile-onset HPP; however, higher values did decrease slightly over time. Mean and median vitamin D values in patients with infantile- and juvenile-onset HPP were relatively consistent over time (Table 1 and FIG. 3).

TABLE 1

Changes from Baseline to Week 24 and last visit for serum $Ca^{2+}$, PTH, phosphate and Vitamin D; pooled safety set overall.

| Parameter Statistic | Baseline | Week 24 | Change from Baseline to Week 24 | Last Visit | Change from Baseline to Last Visit |
|---|---|---|---|---|---|
| Calcium (mmol/L) | | | | | |
| n | 71 | 64 | 64 | 70 | 70 |
| Mean (SD) | 2.540 (0.2727) | 2.487 (0.1580) | −0.055 (0.2459) | 2.504 (0.2109) | −0.039 (0.2693) |
| Median | 2.500 | 2.485 | −0.025 | 2.470 | −0.045 |
| Range | 1.92, 4.03 | 1.82, 2.80 | −1.33, 0.38 | 2.12, 3.67 | −1.33, 0.67 |
| Parathyroid Hormone (pmol/L) | | | | | |
| n | 57 | 61 | 51 | 69 | 56 |
| Mean (SD) | 2.68 (1.813) | 3.41 (3.848) | 0.86 (4.230) | 3.66 (4.988) | 0.73 (2.406) |
| Median | 2.40 | 2.50 | 0.50 | 2.40 | 0.45 |
| Range | 0.6, 8.0 | 0.6, 27.9 | −6.2, 26.7 | 0.6, 38.7 | −4.4, 7.8 |
| Phosphate (mmol/L) | | | | | |
| n | 70 | 63 | 62 | 70 | 69 |
| Mean (SD) | 1.814 (0.3922) | 1.900 (0.3520) | 0.090 (0.3962) | 1.771 (0.2967) | −0.042 (0.3960) |
| Median | 1.870 | 1.970 | 0.025 | 1.760 | −0.090 |
| Range | 0.42, 2.74 | 0.90, 2.50 | −0.51, 1.49 | 1.00, 2.50 | −0.71, 1.23 |
| 25-Hydroxy Vitamin D (pmol/mL) | | | | | |
| n | 68 | 65 | 63 | 67 | 64 |
| Mean (SD) | 76.5 (28.99) | 86.2 (33.58) | 9.8 (35.56) | 78.3 (25.08) | 3.5 (35.32) |
| Median | 77.0 | 80.7 | 4.0 | 75.0 | −1.0 |
| Range | 17, 169 | 23, 212 | −54, 135 | 18, 179 | −83, 91 |

SD = standard deviation.

Example 5

Figure 5:
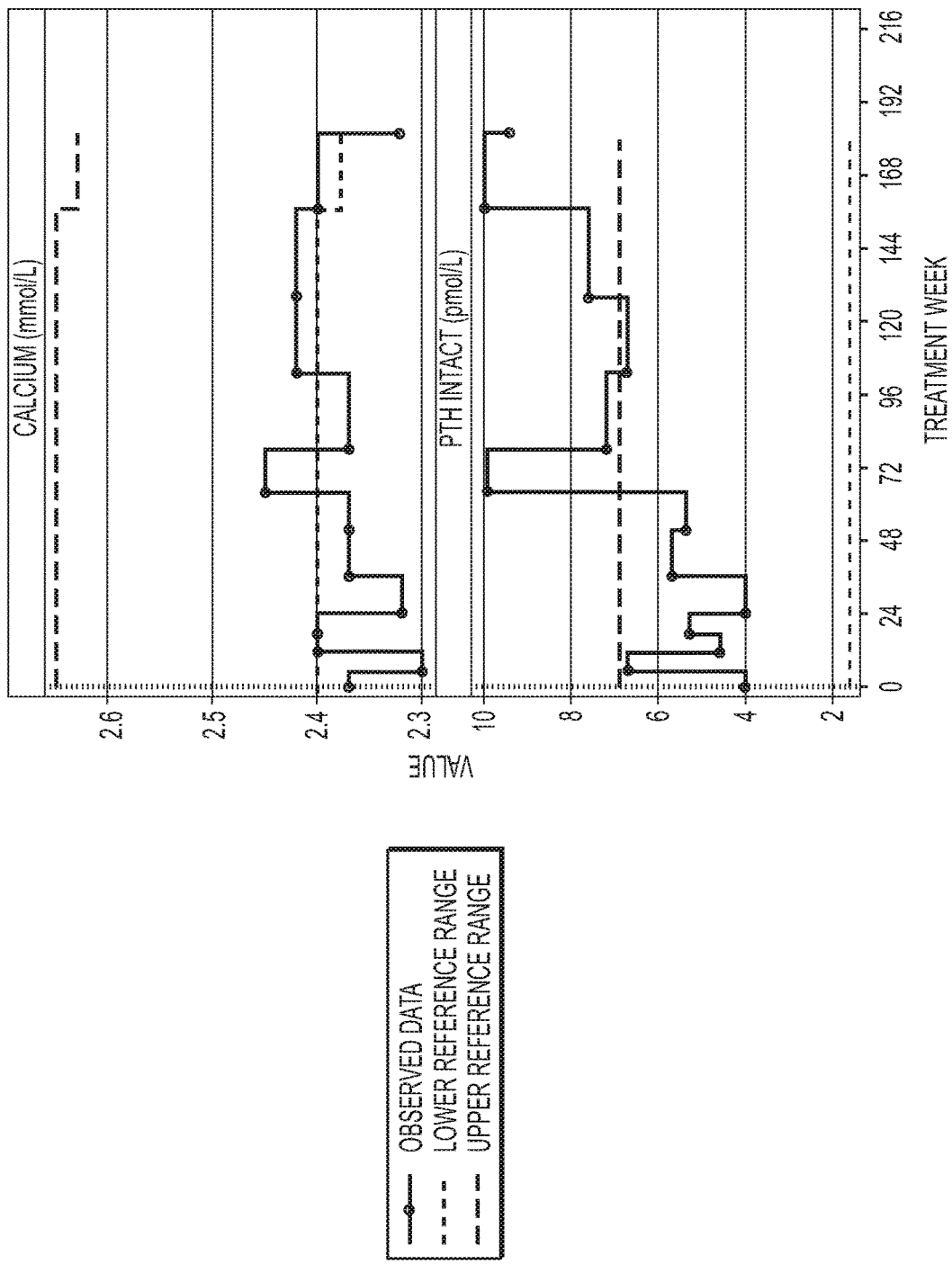
Figure 6:
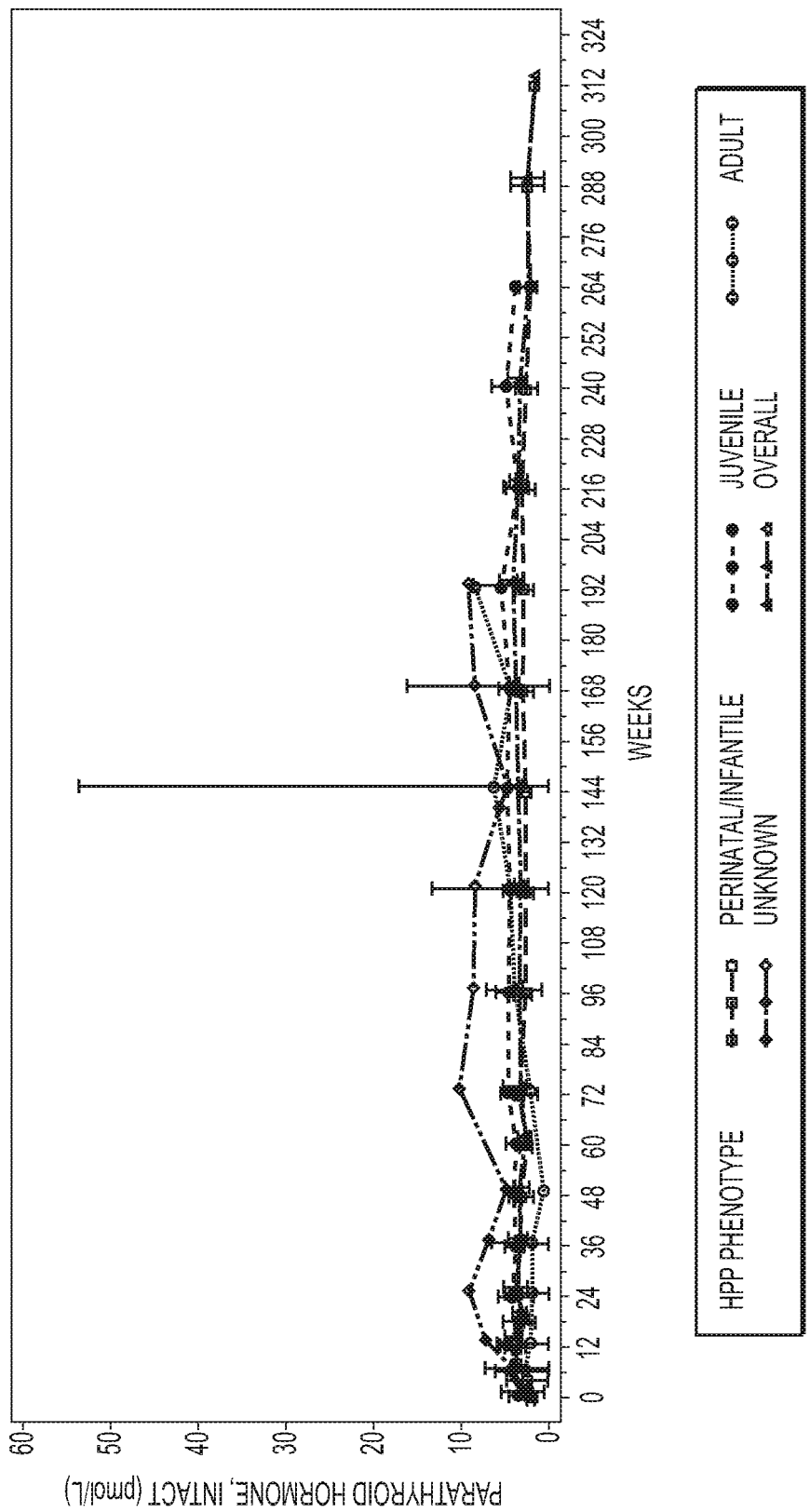
Figure 7:
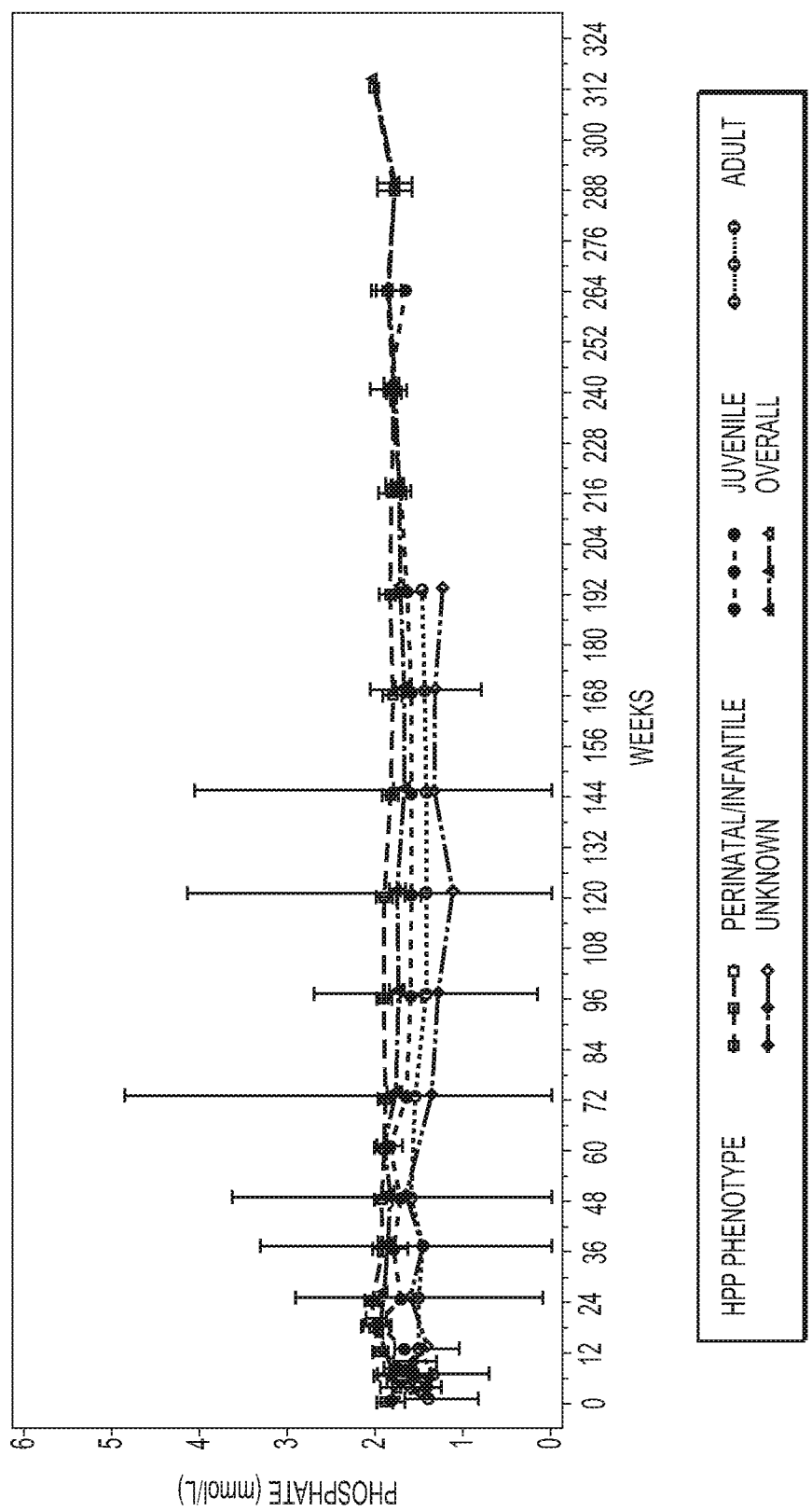
Figure 8:
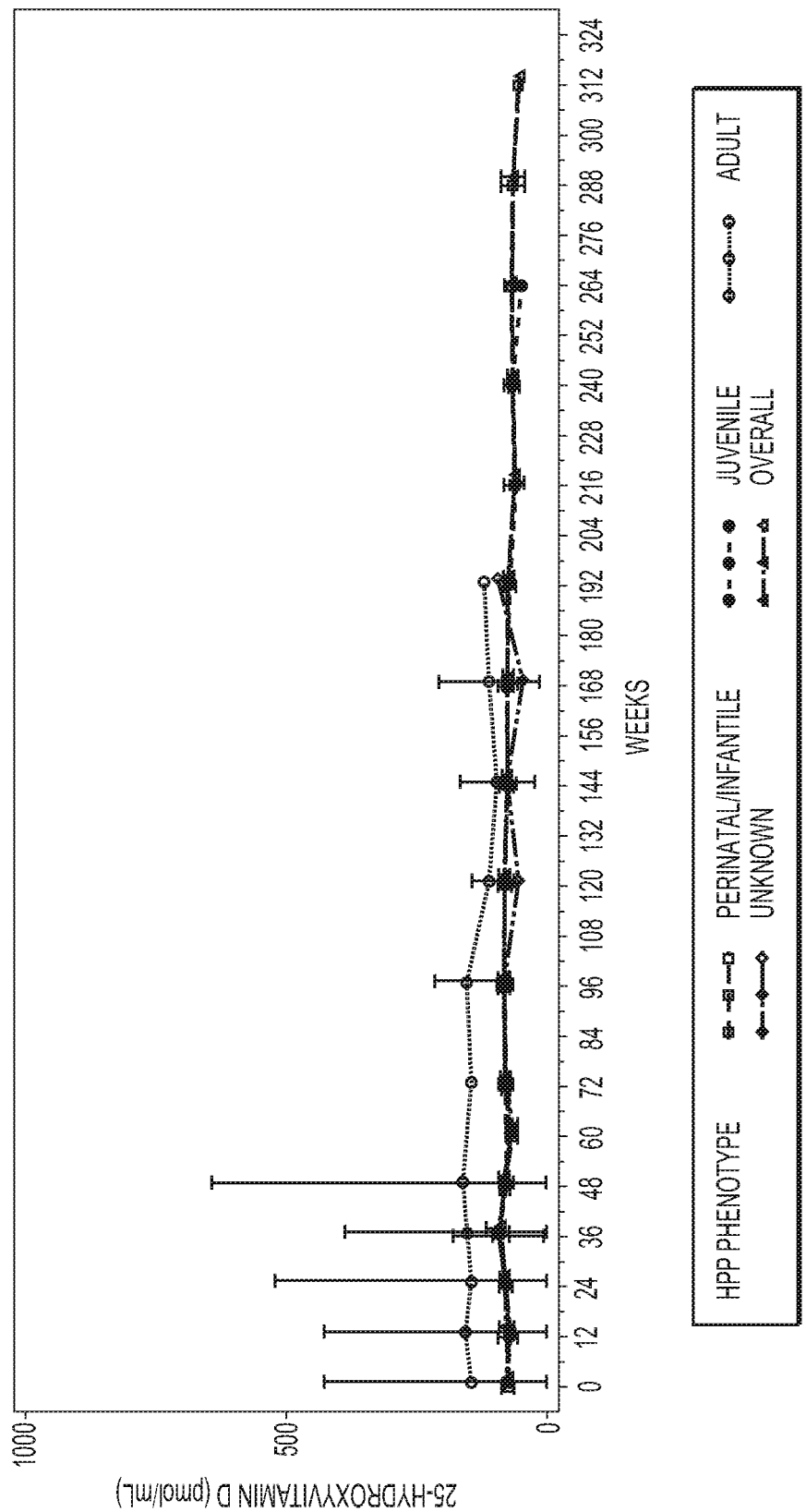
Figure 9:
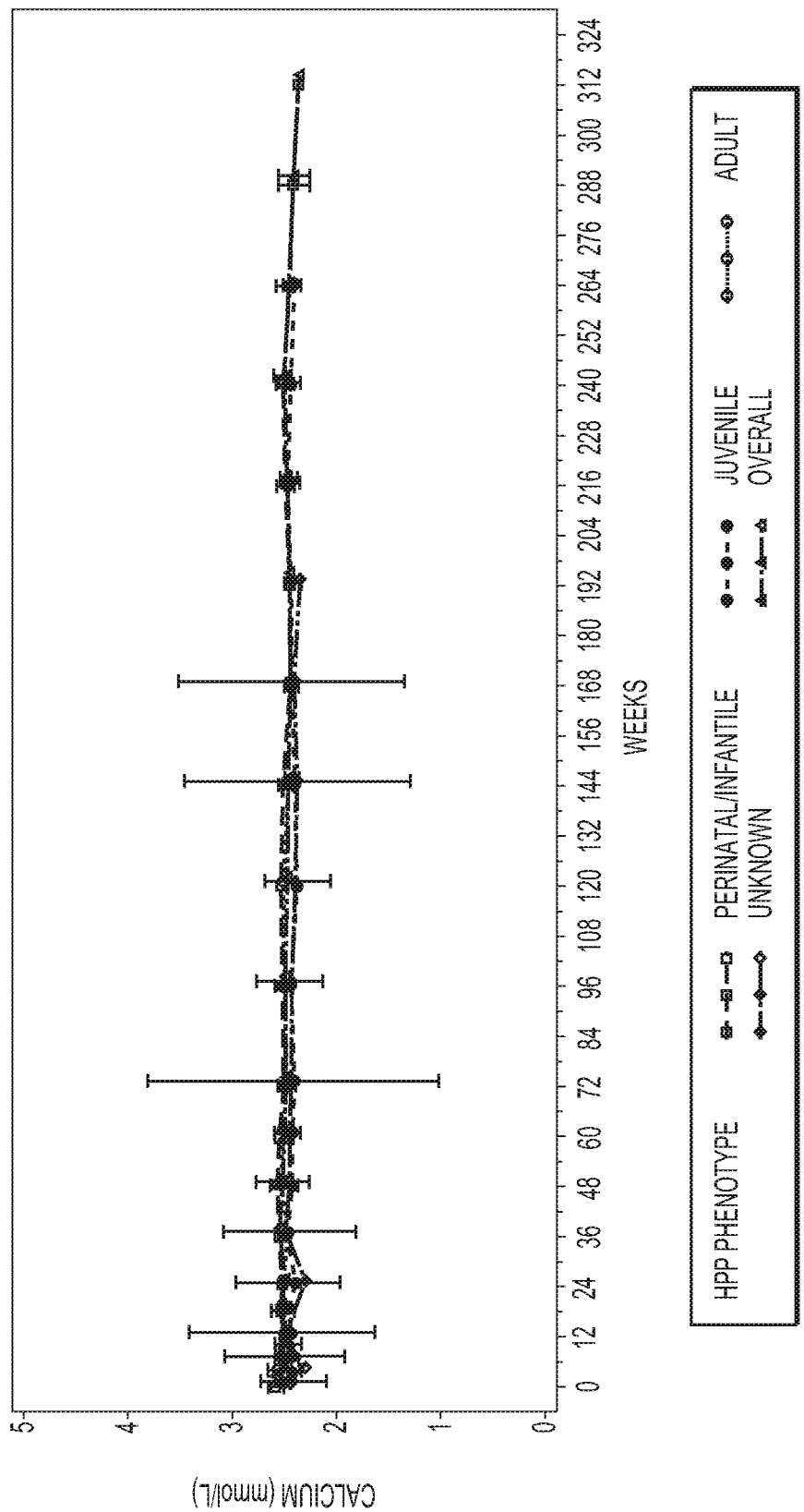
Figure 10:
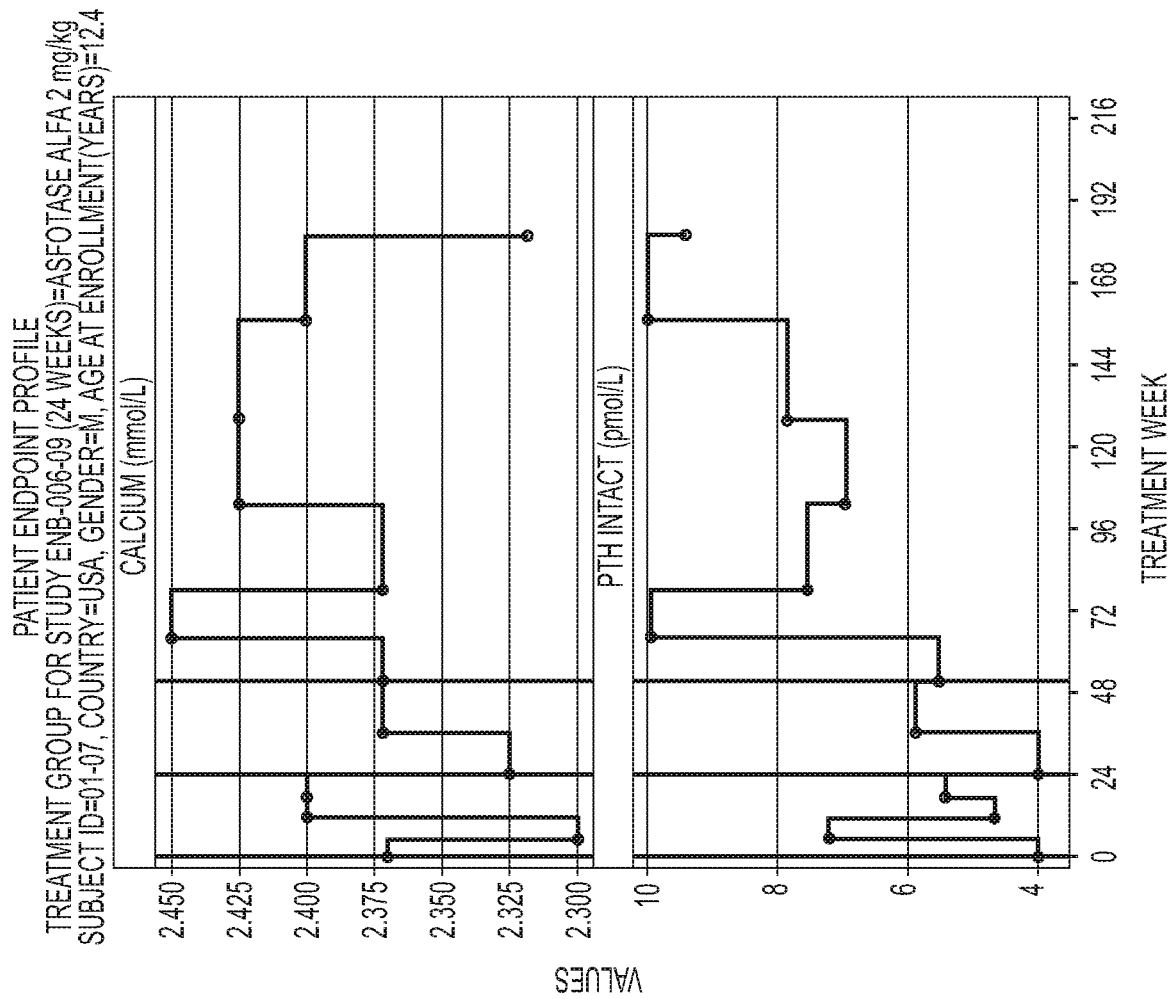
FIG. 10 shows the patient values for calcium (mmol/L) and PTH (pmol/L) as a function of treatment week for the patient of FIG. 5. Vertical lines mark the start and end of 3 mg/kg/week dosing and the start of 6 mg/kg/week dosing.

One patient had a low serum calcium level at Baseline, but upon initiation of asfotase alfa treatment it further decreased, and was responsive to changes in asfotase alfa dosage changes. At Week 24 the dose was reduced from 6 mg/kg/week to 3 mg/kg/week and at Week 48 it was raised to 6 mg/kg/week. During this period PTH levels initially rose but stayed within the normal range up to Week 72, when levels were temporarily elevated above the normal range. Simultaneously, calcium was raised and entered to the normal range. The patient showed signs of radiographic improvement starting at Week 12, although the RGI-C score did not reach 2 or above (meaning substantial improvement in radiographic signs of rickets). At Week 168, serum calcium fell below the normal range and PTH increased above the normal range, at which time six-minute walk test (6MWT) results showed a large drop compared with the previous result at Week 120. See FIG. 5 and FIG. 10.

Example 6

An additional year of data was subsequently collected for the patients contained in Examples 1-5 which demonstrated continuation of the previously described trends, see FIGS. 6-9.

OTHER EMBODIMENTS

It is to be understood that while the present disclosure has been described in conjunction with the detailed description herein; the foregoing description is intended to illustrate and not limit the scope as defined by the appended claims. Other aspects, advantages, and modifications are within the scope of the following claims. References cited in the Specification are herein incorporated by reference in their entireties.

What is claimed is:

1. A method of maintaining calcium homeostasis in a subject treated with an alkaline phosphatase for an alkaline phosphatase deficiency, wherein the alkaline phosphatase is asfotase alfa comprising the amino acid sequence of SEQ ID NO: 1, wherein the subject is determined to have a serum calcium concentration of less than 8.5 mg/dL comprising administering to the subject a therapeutic agent that increases the serum calcium concentration in the subject to 8.5 mg/dL or higher.

2. The method of claim 1, wherein the alkaline phosphatase deficiency is hypophosphatasia.

3. The method of claim 1, wherein the alkaline phosphatase is a tissue non-specific alkaline phosphatase, a placental alkaline phosphatase, an intestinal alkaline phosphatase, an engineered alkaline phosphatase, a fusion protein comprising an alkaline phosphatase moiety, or a chimeric alkaline phosphatase.

4. The method of claim 1, wherein, following administration of the therapeutic agent, the subject is determined to have a serum calcium concentration of higher than 10.5 mg/dL, and the method further comprises administering an additional therapeutic agent that reduces the serum calcium concentration in the subject to 10.5 mg/dL or lower.

5. The method of claim 1, wherein the method further comprises administering calcium or vitamin D to the subject, wherein the subject has a statistically significant low serum concentration of parathyroid hormone.

6. The method of claim 1, wherein the method further comprises administering vitamin D or a functional analog thereof to the subject, wherein the subject has a statistically significant low serum concentration of vitamin D.

7. The method of claim 2, further comprising administering vitamin D to the subject.

8. The method of claim 7, wherein the vitamin D is administered orally, intramuscularly, or intravenously.

9. The method of claim 1, wherein the alkaline phosphatase is administered in a dosage of from about 2 mg/kg/week to 9 mg/kg/week, or a comparable daily dosage.

10. The method of claim 1, wherein the therapeutic agent is calcium gluconate, or calcium chloride.

11. The method of claim 1, wherein the therapeutic agent is vitamin D or a functional vitamin D analog.

12. The method of claim 1, wherein the therapeutic agent is parathyroid hormone (PTH) or a functional PTH analog.

13. The method of claim 4, wherein the third therapeutic agent is wherein the therapeutic agent is a calcimimetic.

14. The method of claim 13, wherein the calcimimetic is cinacalcet.

15. The method of claim 4, wherein the additional therapeutic agent is a bisphosphonate.

16. The method of claim 4, wherein the additional therapeutic agent is prednisone.

17. The method of claim 4, wherein the additional therapeutic agent is an intravenous fluid.

18. The method of claim 4, wherein the additional therapeutic agent is a diuretic.

19. The method of claim 2, further comprising administering vitamin K to the subject.

20. The method of claim 2, further comprising administering vitamin B to the subject.

21. The method of claim 2, further comprising administering a multivitamin to the subject.

22. The method of claim 1, wherein the subject has a serum calcium concentration of 7.0 mg/dL or lower to 0.5 mg/dL or lower.

* * * * *

```
                        SEQUENCE LISTING

<160> NUMBER OF SEQ ID NOS: 1

<210> SEQ ID NO 1
<211> LENGTH: 726
<212> TYPE: PRT
<213> ORGANISM: Artificial Sequence
<220> FEATURE:
<223> OTHER INFORMATION: Synthetic Construct

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320
```

```
His Gly His His Glu Gly Lys Ala Lys Gln Ala Leu His Glu Ala Val
                325                 330                 335
Glu Met Asp Arg Ala Ile Gly Gln Ala Gly Ser Leu Thr Ser Ser Glu
                340                 345                 350
Asp Thr Leu Thr Val Val Thr Ala Asp His Ser His Val Phe Thr Phe
                355                 360                 365
Gly Gly Tyr Thr Pro Arg Gly Asn Ser Ile Phe Gly Leu Ala Pro Met
            370                 375                 380
Leu Ser Asp Thr Asp Lys Lys Pro Phe Thr Ala Ile Leu Tyr Gly Asn
385                 390                 395                 400
Gly Pro Gly Tyr Lys Val Val Gly Gly Glu Arg Glu Asn Val Ser Met
                405                 410                 415
Val Asp Tyr Ala His Asn Asn Tyr Gln Ala Gln Ser Ala Val Pro Leu
                420                 425                 430
Arg His Glu Thr His Gly Gly Glu Asp Val Ala Val Phe Ser Lys Gly
            435                 440                 445
Pro Met Ala His Leu Leu His Gly Val His Glu Gln Asn Tyr Val Pro
        450                 455                 460
His Val Met Ala Tyr Ala Ala Cys Ile Gly Ala Asn Leu Gly His Cys
465                 470                 475                 480
Ala Pro Ala Ser Ser Leu Lys Asp Lys Thr His Thr Cys Pro Pro Cys
                485                 490                 495
Pro Ala Pro Glu Leu Leu Gly Gly Pro Ser Val Phe Leu Phe Pro Pro
            500                 505                 510
Lys Pro Lys Asp Thr Leu Met Ile Ser Arg Thr Pro Glu Val Thr Cys
        515                 520                 525
Val Val Val Asp Val Ser His Glu Asp Pro Glu Val Lys Phe Asn Trp
    530                 535                 540
Tyr Val Asp Gly Val Glu Val His Asn Ala Lys Thr Lys Pro Arg Glu
545                 550                 555                 560
Glu Gln Tyr Asn Ser Thr Tyr Arg Val Val Ser Val Leu Thr Val Leu
                565                 570                 575
His Gln Asp Trp Leu Asn Gly Lys Glu Tyr Lys Cys Lys Val Ser Asn
            580                 585                 590
Lys Ala Leu Pro Ala Pro Ile Glu Lys Thr Ile Ser Lys Ala Lys Gly
        595                 600                 605
Gln Pro Arg Glu Pro Gln Val Tyr Thr Leu Pro Pro Ser Arg Glu Glu
        610                 615                 620
Met Thr Lys Asn Gln Val Ser Leu Thr Cys Leu Val Lys Gly Phe Tyr
625                 630                 635                 640
Pro Ser Asp Ile Ala Val Glu Trp Glu Ser Asn Gly Gln Pro Glu Asn
                645                 650                 655
Asn Tyr Lys Thr Thr Pro Pro Val Leu Asp Ser Asp Gly Ser Phe Phe
            660                 665                 670
Leu Tyr Ser Lys Leu Thr Val Asp Lys Ser Arg Trp Gln Gln Gly Asn
        675                 680                 685
Val Phe Ser Cys Ser Val Met His Glu Ala Leu His Asn His Tyr Thr
        690                 695                 700
Gln Lys Ser Leu Ser Leu Ser Pro Gly Lys Asp Ile Asp Asp Asp Asp
705                 710                 715                 720
Asp Asp Asp Asp Asp
                725
```